(12) United States Patent
Mitchell et al.

(10) Patent No.: US 7,399,753 B2
(45) Date of Patent: Jul. 15, 2008

(54) TRANS-SPLICING MEDIATED PHOTODYNAMIC THERAPY

(75) Inventors: Lloyd G. Mitchell, Bethesda, MD (US); Edward Otto, Great Falls, VA (US); Carl R. Merril, Bethesda, MD (US)

(73) Assignee: Virxsys Corporation, Gaithersburg, MD (US)

(*) Notice: Subject to any disclaimer, the term of this patent is extended or adjusted under 35 U.S.C. 154(b) by 442 days.

(21) Appl. No.: 10/658,617

(22) Filed: Sep. 9, 2003

(65) Prior Publication Data

US 2004/0132181 A1    Jul. 8, 2004

(51) Int. Cl.
C12N 5/10      (2006.01)
C12N 15/87     (2006.01)
C12N 15/63     (2006.01)
C12N 15/66     (2006.01)
C12N 15/00     (2006.01)
A61K 31/711    (2006.01)
C12N 15/861    (2006.01)

(52) U.S. Cl. .......... 514/44; 435/325; 435/455; 435/69.1; 435/91.1; 435/91.3

(58) Field of Classification Search .......... 435/320.1, 435/325, 366, 455, 456, 69.1; 536/23.1, 536/23.2, 23.4, 24.1; 424/93.1, 93.2, 93.6; 514/44

See application file for complete search history.

(56) References Cited

U.S. PATENT DOCUMENTS

2004/0038403 A1*  2/2004  Otto ................... 435/456
2004/0058344 A1*  3/2004  Mitchell et al. ........ 435/6

OTHER PUBLICATIONS

Liu et al., Nature Biotechnology, Jan. 2002, vol. 20, pp. 47-52.*
Puttaraju et al., Nature Biotechnology, 1999, vol. 17, pp. 246-252.*

* cited by examiner

*Primary Examiner*—David Guzo
(74) *Attorney, Agent, or Firm*—Konstantina M. Katcheves; Saul Ewing LLP

(57) ABSTRACT

The present invention provides methods and compositions for conferring selective death on cells expressing a specific target precursor messenger RNA (selective target pre-mRNA). The compositions of the invention include pre-trans-splicing molecules (PTMs) designed to interact with a target precursor messenger RNA molecule (target pre-mRNA) expressed within a cell and mediate a trans-splicing reaction resulting in the generation of a novel chimeric mRNA molecule (chimeric mRNA) capable of encoding a light producing protein or enzyme. Cell death is further mediated by the presence of a photosensitizer which upon photoactivation produces cytotoxicity.

15 Claims, 31 Drawing Sheets

Figure 3:
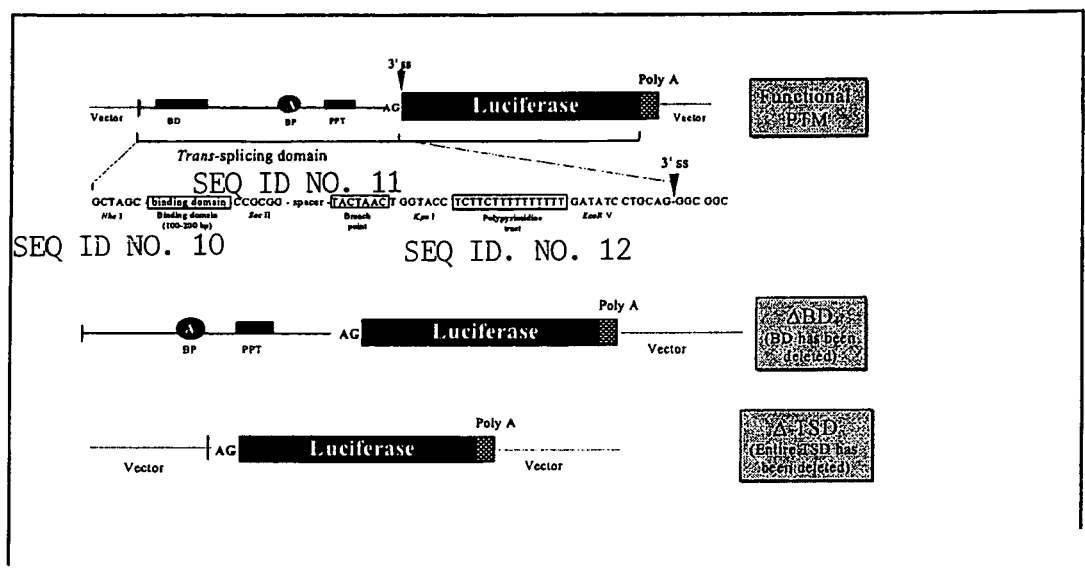

Figure 3. Schematic diagrams of the pre-mRNA targets: (a) HPV type 16, (b) β-HCG6 and (c) EGFR.

Figure 1A:
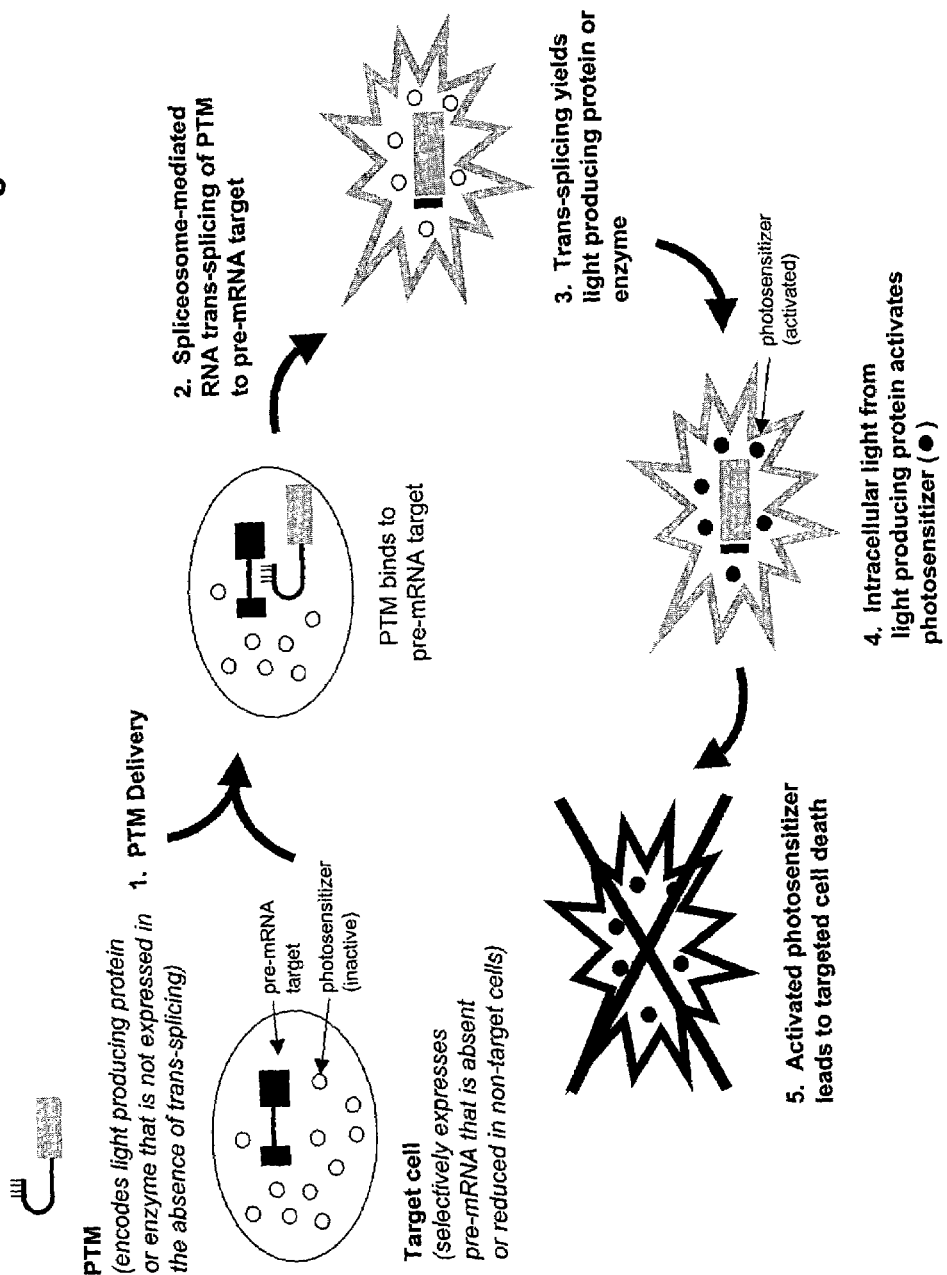

Fig. 1A. Schematic drawing of mini-gene target

SEQ ID NO. 16

Imaging of gene expression using full-length reporter PTM

Structure of a full-length imaging PTM (Luc-PTM38)

Imaging Gene Expression (*In vivo*)

Target + PTM used for the above study

SEQUENCE LISTING

```
<160> NUMBER OF SEQ ID NOS: 21

<210> SEQ ID NO 1
<211> LENGTH: 8
<212> TYPE: RNA
<213> ORGANISM: Artificial
<220> FEATURE:
<223> OTHER INFORMATION: Chemically Synthesized

<400> SEQUENCE: 1 agguragu                                                            8
```

```
<210> SEQ ID NO 2
<211> LENGTH: 7
<212> TYPE: RNA
<213> ORGANISM: Artificial
<220> FEATURE:
<223> OTHER INFORMATION: Chemically Synthesized
<220> FEATURE:
<221> NAME/KEY: misc_feature
<222> LOCATION: (2)..(2)
<223> OTHER INFORMATION: n is a, c, g, or u

<400> SEQUENCE: 2 ynyurac                                                              7

<210> SEQ ID NO 3
<211> LENGTH: 7
<212> TYPE: RNA
<213> ORGANISM: Artificial
<220> FEATURE:
<223> OTHER INFORMATION: Chemically Synthesized

<400> SEQUENCE: 3 uacuaac                                                              7

<210> SEQ ID NO 4
<211> LENGTH: 7
<212> TYPE: RNA
<213> ORGANISM: Artificial
<220> FEATURE:
<223> OTHER INFORMATION: Chemically Synthesized

<400> SEQUENCE: 4 uacuaac                                                              7

<210> SEQ ID NO 5
<211> LENGTH: 8
<212> TYPE: DNA
<213> ORGANISM: Artificial
<220> FEATURE:
<223> OTHER INFORMATION: Chemically Synthesized

<400> SEQUENCE: 5 ygtgttyy                                                             8

<210> SEQ ID NO 6
<211> LENGTH: 7
<212> TYPE: RNA
<213> ORGANISM: Artificial
<220> FEATURE:
<223> OTHER INFORMATION: Chemically Synthesized

<400> SEQUENCE: 6 uacuaac                                                              7

<210> SEQ ID NO 7
<211> LENGTH: 29
<212> TYPE: DNA
<213> ORGANISM: Artificial
<220> FEATURE:
<223> OTHER INFORMATION: Chemically Synthesized

<400> SEQUENCE: 7
aagcttttac tgctcgttct tcagcacgc                                     29

<210> SEQ ID NO 8
```

```
<211> LENGTH: 20
<212> TYPE: DNA
<213> ORGANISM: Artificial
<220> FEATURE:
<223> OTHER INFORMATION: Chemically Synthesized

<400> SEQUENCE: 8
cagggtcgga ctcgatgaac                                              20

<210> SEQ ID NO 9
<211> LENGTH: 21
<212> TYPE: DNA
<213> ORGANISM: Artificial
<220> FEATURE:
<223> OTHER INFORMATION: Chemically Synthesized

<400> SEQUENCE: 9
ggatatcgcc ctgatcaaga g                                            21

<210> SEQ ID NO 10
<211> LENGTH: 6
<212> TYPE: DNA
<213> ORGANISM: Artificial
<220> FEATURE:
<223> OTHER INFORMATION: Chemically Synthesized

<400> SEQUENCE: 10 gctagc                                                              6

<210> SEQ ID NO 11
<211> LENGTH: 6
<212> TYPE: RNA
<213> ORGANISM: Artificial
<220> FEATURE:
<223> OTHER INFORMATION: Chemically Synthesized

<400> SEQUENCE: 11 ccgcgg                                                              6

<210> SEQ ID NO 12
<211> LENGTH: 47
<212> TYPE: DNA
<213> ORGANISM: Artificial
<220> FEATURE:
<223> OTHER INFORMATION: Chemically Synthesized

<400> SEQUENCE: 12
tactaactgg tacctcttct ttttttttg atatcctgca gggcggc                 47

<210> SEQ ID NO 13
<211> LENGTH: 6
<212> TYPE: DNA
<213> ORGANISM: Artificial
<220> FEATURE:
<223> OTHER INFORMATION: Chemically Synthesized

<400> SEQUENCE: 13 gctagc                                                              6

<210> SEQ ID NO 14
<211> LENGTH: 6
<212> TYPE: RNA
<213> ORGANISM: Artificial
<220> FEATURE:
<223> OTHER INFORMATION: Chemically Synthesized

<400> SEQUENCE: 14
``` ccgcgg                                                              6

<210> SEQ ID NO 15
<211> LENGTH: 47
<212> TYPE: DNA
<213> ORGANISM: Artificial
<220> FEATURE:
<223> OTHER INFORMATION: Chemically Synthesized

<400> SEQUENCE: 15
tactaactgg tacctcttct ttttttttg atatcctgca gggcggc                   47

<210> SEQ ID NO 16
<211> LENGTH: 65
<212> TYPE: DNA
<213> ORGANISM: Artificial
<220> FEATURE:
<223> OTHER INFORMATION: Chemically Synthesized

<400> SEQUENCE: 16
ctcctggcct cgcgagatcc ctctcgttaa gggaggcaag cccgacgtcg tccagattgt    60
ccgca                                                                65

<210> SEQ ID NO 17
<211> LENGTH: 6
<212> TYPE: DNA
<213> ORGANISM: Artificial
<220> FEATURE:
<223> OTHER INFORMATION: Chemically Synthesized

<400> SEQUENCE: 17 ctgcag                                                               6

<210> SEQ ID NO 18
<211> LENGTH: 71
<212> TYPE: DNA
<213> ORGANISM: Artificial
<220> FEATURE:
<223> OTHER INFORMATION: Chemically Synthesized

<400> SEQUENCE: 18
ccgcggaaca ttattataac gttgctcgaa tactaactgg tacctcttct ttttttttg    60 atatcctgca g                                                         71

<210> SEQ ID NO 19
<211> LENGTH: 22
<212> TYPE: DNA
<213> ORGANISM: Artificial
<220> FEATURE:
<223> OTHER INFORMATION: Chemically Synthesized

<400> SEQUENCE: 19
ctcgagcacc gatatcgtaa ct                                             22

<210> SEQ ID NO 20
<211> LENGTH: 36
<212> TYPE: DNA
<213> ORGANISM: Artificial
<220> FEATURE:
<223> OTHER INFORMATION: Chemically Synthesized

<400> SEQUENCE: 20
tactaactct cttctttttt ttttgataac caggct                              36

```
<210> SEQ ID NO 21
<211> LENGTH: 35
<212> TYPE: DNA
<213> ORGANISM: Artificial
<220> FEATURE:
<223> OTHER INFORMATION: Chemically Synthesized

<400> SEQUENCE: 21
gaacacctca ctacatacat aacagttaac ccgct                                35
```

TRANS-SPLICING MEDIATED PHOTODYNAMIC THERAPY

1. INTRODUCTION

The present invention provides methods and compositions for conferring selective death on cells expressing a specific target precursor messenger RNA (selective target pre-mRNA). The compositions of the invention include pre-trans-splicing molecules (PTMs) designed to interact with a target precursor messenger RNA molecule (target pre-mRNA) expressed within a cell and mediate a trans-splicing reaction resulting in the generation of a novel chimeric mRNA molecule (chimeric mRNA) capable of encoding a light producing protein or enzyme. Cell death is further mediated by the presence of a photosensitizer which upon photoactivation produces cytotoxicity.

The methods and compositions of the invention may be used to treat a variety of different diseases where the goal is selective destruction of one or more specific cell types. For example, the present invention provides methods and compositions for conferring selective cell death on cancer cells expressing a specific target precursor messenger RNA molecules (cancer cell selective target pre-mRNAs). Such compositions include pre-trans-splicing molecules (PTMs) designed to interact with one or more cancer cell selective target pre-mRNA and mediate a trans-splicing reaction resulting in the generation of novel chimeric mRNA molecules (chimeric mRNA) capable of encoding a light producing protein or an enzyme that catalyzes the conversion of a substrate in a light producing chemical reaction. Alternatively, the present invention may be utilized to confer selective cell death on cells infected with a pathogenic microorganism. In such instances, PTMs are designed to interact with one or more target pre-mRNA encoded by the pathogenic microorganism, or induced within the cells of a subject infected with a pathogenic microorganism and encode a light producing protein or enzyme. Upon successful trans-splicing between the target pre-mRNA and the PTM, the light producing protein or enzyme is expressed thereby providing the required complementing activity necessary for activation of a cytotoxic photosensitizer.

2. BACKGROUND OF THE INVENTION

DNA sequences in the chromosome are transcribed into pre-mRNAs which contain coding regions (exons) and generally also contain intervening non-coding regions (introns). Introns are removed from pre-mRNAs in a precise process referred to as splicing. In most cases, the splicing reaction occurs within the same pre-mRNA molecule, which is termed cis-splicing. Splicing between two independently transcribed pre-mRNAs is termed trans-splicing. Trans-splicing was first discovered in trypanosomes (Sutton & Boothroyd, 1986, Cell 47:527; Murphy et al., 1986, Cell 47:517) and subsequently in nematodes (Krause & Hirsh, 1987, Cell 49:753); flatworms (Rajkovic et al., 1990, Proc. Nat'l. Acad. Sci. USA, 87:8879; Davis et al., 1995, J. Biol. Chem. 270:21813) and in plant mitochondria (Malek et al., 1997, Proc. Nat'l. Acad. Sci. USA 94:553). In the parasite *Trypanosoma brucei*, all mRNAs acquire a splice leader (SL) RNA at their 5' termini by trans-splicing. A 5' leader sequence is also trans-spliced onto some genes in *Caenorhabditis elegans*. This mechanism is appropriate for adding a single common sequence to many different transcripts.

The mechanism of spliced leader trans-splicing, which is nearly identical to that of conventional cis-splicing, proceeds via two phosphoryl transfer reactions. The first causes the formation of a 2'-5' phosphodiester bond producing a 'Y' shaped branched intermediate, equivalent to the lariat intermediate in cis-splicing. The second reaction, exon ligation, proceeds as in conventional cis-splicing. In addition, sequences at the 3' splice site and some of the snRNPs which catalyze the trans-splicing reaction, closely resemble their counterparts involved in cis-splicing.

Trans-splicing may also refer to a different process, where an intron of one pre-mRNA interacts with an intron of a second pre-mRNA, enhancing the recombination of splice sites between two conventional pre-mRNAs. This type of trans-splicing was postulated to account for transcripts encoding a human immunoglobulin variable region sequence linked to the endogenous constant region in a transgenic mouse (Shimizu et al., 1989, Proc. Nat'l. Acad. Sci. USA 86:8020). In addition, trans-splicing of c-myb pre-RNA has been demonstrated (Vellard, M. et al. Proc. Nat'l. Acad. Sci., 1992 89:2511-2515), trans-spliced RNA transcripts from SV40 have been detected in cultured cells and nuclear extracts (Eul et al., 1995, EMBO. J. 14:3226) and more recently, the transcript from the p450 gene in human liver has been shown to be trans-spliced (Finta et al., 2002, J. Biol Chem 22:5882-5890). However, in general, naturally occurring trans-splicing of mammalian pre-mRNAs is thought to be an exceedingly rare event.

In vitro trans-splicing has been used as a model system to examine the mechanism of splicing by several groups (Konarska & Sharp, 1985, Cell 46:165-171 Solnick, 1985, Cell 42:157; Chiara & Reed, 1995, Nature 375:510). Reasonably efficient trans-splicing (30% of cis-spliced analog) was achieved between RNAs capable of base pairing to each other, splicing of RNAs not tethered by base pairing was further diminished by a factor of 10. Other in vitro trans-splicing reactions not requiring obvious RNA-RNA interactions among the substrates were observed by Chiara & Reed (1995, Nature 375:510), Bruzik J. P. & Maniatis, T. (1992, Nature 360:692) and Bruzik J. P. and Maniatis, T., (1995, Proc. Nat'l. Acad. Sci. USA 92:7056-7059). These reactions occur at relatively low frequencies and require specialized elements, such as a downstream 5' splice site or exonic splicing enhancers.

U.S. Pat. Nos. 6,083,702, 6,013,487 and 6,280,978 describe the use of PTMs to mediate a trans-splicing reaction by contacting a target precursor mRNA to generate novel chimeric mRNAs. The resulting RNA can encode any gene product including a protein of therapeutic value to the cell or host organism, a toxin, such as Diptheria toxin subunit A, which causes killing of the specific cells or a novel protein not normally present in cells. The PTMs can also be engineered for the production of chimeric proteins including those encoding reporter molecules useful to image gene expression in vivo in real time or to add peptide affinity purification tags which can be used to purify and identify proteins expressed in a specific cell type.

Photodynamic therapy (PDT) of cancer uses light excitation of a photosensitive substance to produce oxygen-related cytotoxic intermediates, such as singlet oxygen or free radicals (Dougherty et al., 1993, Photochem. Photobiol. 58:895-900; Hopper et al., 2000, Lancet Oncol. 1:212-219; Ochsner et al., 1997, J. Photochem. Photobiol. B. Biol 39:1-18, Fuchs et al., 1998, Biol. Med. 24:835-847). For example, the use of $CL^4$ for the excitation of the photosensitizer hypercin has been used for the in vitro inactivation of the equine infectious anemia virus (Carpenter, S. et al. 1994, Proc. Natl. Acad. Sci. USA 91:12273-12277). Additionally, Theodossis et al., described the in vitro photodynamic effect of rose bengal activated by intracellular generation of light generated by the oxidation of the chemiluminescent substrate luciferin, in luciferase-transfected NIH 3T3 murine fibroblasts (Theodossis et al., 2003, Cancer Research 63:1818-1821).

PDT involves the use of two individual components that combine to induce cytotoxicity in an oxygen dependent manner. The first component of PDT is a photosensitizer molecule that usually enters cells and/or tissues non-specifically. The second component involves the localized administration of light of a specific wavelength that is capable of activating the photosensitizer. Once activated the photosensitizer transfers energy from the light to molecular oxygen, thereby generating reactive oxygen species (ROS), such as singlet oxygen and free radicals. Such ROS mediate cellular toxicity. Photosensitizers may also undergo photochemical reactions that do not use oxygen as an intermediate, such as compounds that result in photoaddition to DNA. As used herein, the term photosensitizer includes, but is not limited to, other chemicals that are activated upon exposure to light. Such photosensitizers are known to those skilled in the art and the examples set forth herein are non-limiting.

Although photodynamic therapy use is desirable because of its limited side effects, its main disadvantages are the poor accessibility of light to certain tissues and the problem of restricting the delivery of light primarily to the target cells. The present invention provides methods and compositions for targeted expression of light producing enzymes in the desired cell types and in cells that otherwise are inaccessible to light, thereby providing a method for use of photodynamic therapy for the specific destruction of targeted cells. Specifically, the invention provides PTM molecules that are designed to interact with one or more cell selective target pre-mRNA species and mediate trans-splicing reactions resulting in the generation of chimeric mRNA molecules capable of encoding light producing enzyme or protein. The expression of the light producing enzyme or protein permits activation of a co-localized photosensitizer leading to death of the selected cell. The present invention provides a system for targeting cancer cell destruction. In addition, the invention provides a system for targeting selective cell death to cells infected with pathogenic microorganisms, or, cell death in instances where the activity of a particular cell type leads to disease.

3. SUMMARY OF THE INVENTION

The present invention provides methods and compositions for conferring selective death on cells expressing a specific target precursor messenger RNA (selective target pre-mRNAs). The compositions of the invention include pre-trans-splicing molecules (PTMs) designed to interact with one or more selective target pre-mRNA and mediate a trans-splicing reaction resulting in the generation of novel chimeric mRNA molecules (chimeric mRNA) capable of encoding light producing proteins or enzymes. Light producing proteins include those molecules capable of photoactivating a photosensitizer sufficient to result in formation of cytotoxic intermediates, including cytotoxic oxygen related-intermediates. Light producing proteins include those capable of fluorescence, FRET (fluorescent resonance energy transfer), and phosphorescence. Upon successful trans-splicing between the target pre-mRNA and the PTM, the light producing proteins or enzymes are expressed thereby providing the activity necessary for activation of the photosensitizer. Such activation leads to cell death, thereby targeting selective destruction of specific cells (FIG. 1A).

The present invention provides methods and compositions for conferring selective death on cancer cells expressing specific target precursor messenger RNA molecules (cancer cell selective target pre-mRNAs). The compositions of the invention PTMs are designed to interact with one or more cancer cell selective target pre-mRNA and mediate trans-splicing reactions resulting in the generation of novel chimeric mRNA molecules (chimeric mRNA) capable of encoding a light producing protein or enzyme. The portion of the target pre-mRNA trans-spliced to the PTM provides the signal sequences necessary for translation of the chimeric mRNA molecule. The portion of the PTM trans-spliced to the target pre-mRNA provides sequences encoding light producing enzymes that provide essential activity necessary for activation of cytotoxic photo sensitizers.

The methods and compositions of the invention provide a means for selective destruction of cancer cells within a tumor. Since the viability of tumor cells relies on the supply of nutrients via the bloodstream, targeting of cells of the vascular system may also be used to treat cancer. In such instances, the selective target pre-mRNA is a pre-mRNA expressed in the cells in newly created regions of the vascular system. Thus, the present invention provides methods and compositions for treating a variety of different cancers including but not limited to, breast, prostate, bladder, pancreatic or liver cancer.

In addition the present invention provides methods and compositions for conferring selective death on cells expressing mRNAs produced by a pathogenic infectious agent. In such instances the PTM is designed to interact with one or more target pre-mRNAs produced by the pathogenic infective agent. The portion of the target pre-mRNA produced by, or in response to, the pathogen and trans-spliced to the PTM provides the signal sequences necessary for translation of the chimeric molecule. The portion of the PTM trans-spliced to the target pre-mRNA provides sequences encoding the light producing proteins or enzymes that provide an essential activity necessary for activation of a cytotoxic photosensitizer. The methods and compositions of the invention may be utilized for selective destruction of infected cells.

In yet another embodiment of the invention, the methods and compositions of the invention may be used for conferring cell death in a subject where the activity of that cell leads to a disease state, for example, an immune or hormonal disorder.

4. BRIEF DESCRIPTION OF THE DRAWINGS

Figure 1B:
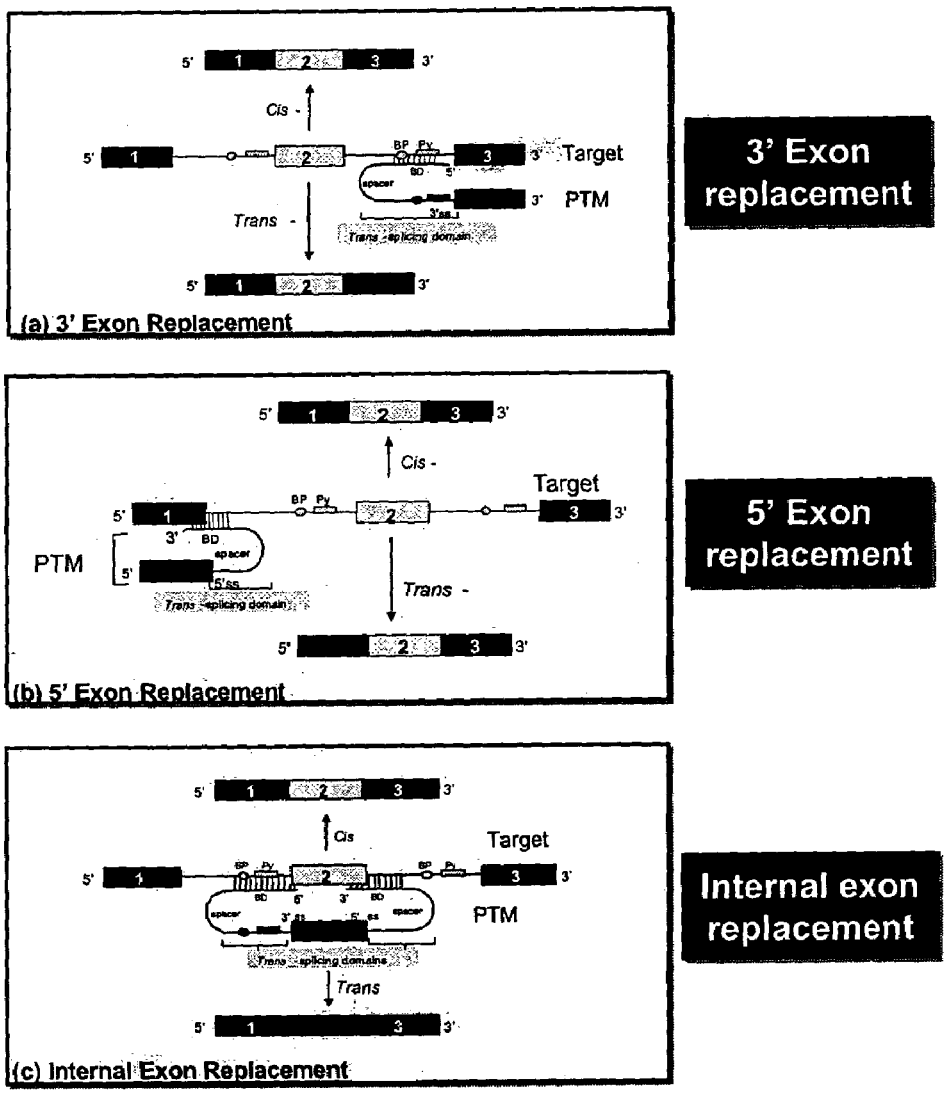

FIG. 1A. Schematic representation of trans-splicing mediated photodynamic therapy FIG. 1B. Schematic representation of different trans-splicing reactions. (a) Trans-splicing reactions between the target pre-mRNA 5' splice site and PTMs 3' splice site; (b) trans-splicing reactions between the target pre-mRNA 3' splice site and PTM's 5' splice site and (c) replacement of internal exon by double trans-splicing reaction in which the PTM carries both 3' and 5' splice sites, each of which trans-splice into a corresponding target pre-mRNA splice site. BD, binding domains; BP, branchpoint sequence; PPT, polypyrimidine tract and ss, splice sites.

Figure 2:
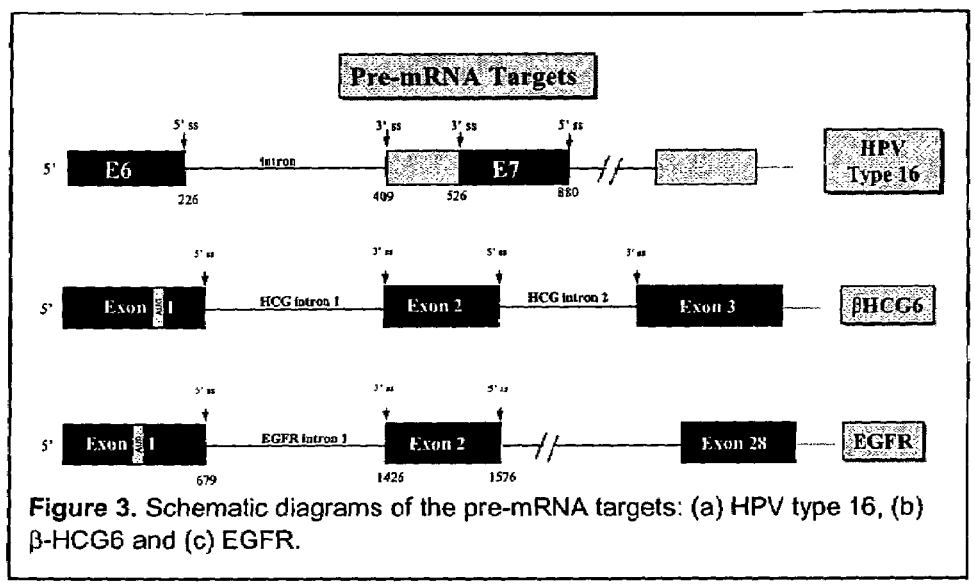

FIG. 2. Schematic diagrams of the pre-mRNA targets; (a) HPV type 16 (b) β-HCG6 and (c) EGFR.

FIG. 3. Schematic diagrams of a prototype PTM and splice mutants showing the important structural elements of trans-splicing domain, (SEQ ID NO:12). BD, binding domain; BP, branchpoint and PPT, polypyrimidine tract. Unique restriction sites in the trans-splicing domain are indicated.

Figure 4:
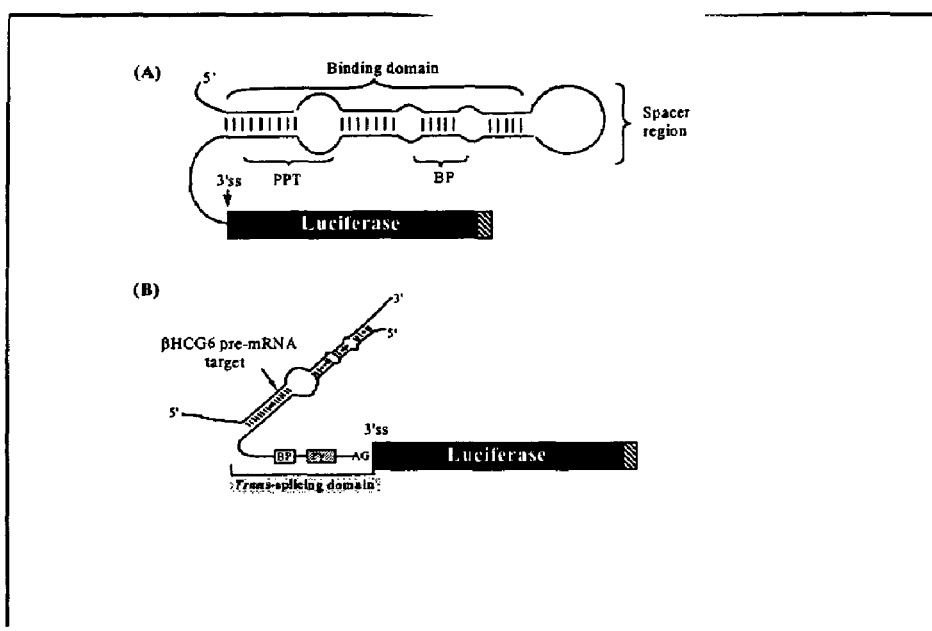

FIG. 4. Illustration of safety mechanism. (a) Schematic diagram of the safety PTM showing the intra-molecular base-paired stem-loop structure designed to cover the 3' splice elements from splicing factors. (b) Diagram of a safety PTM in open configuration after binding to the β-HCG6 pre-mRNA target.

Figure 5A:
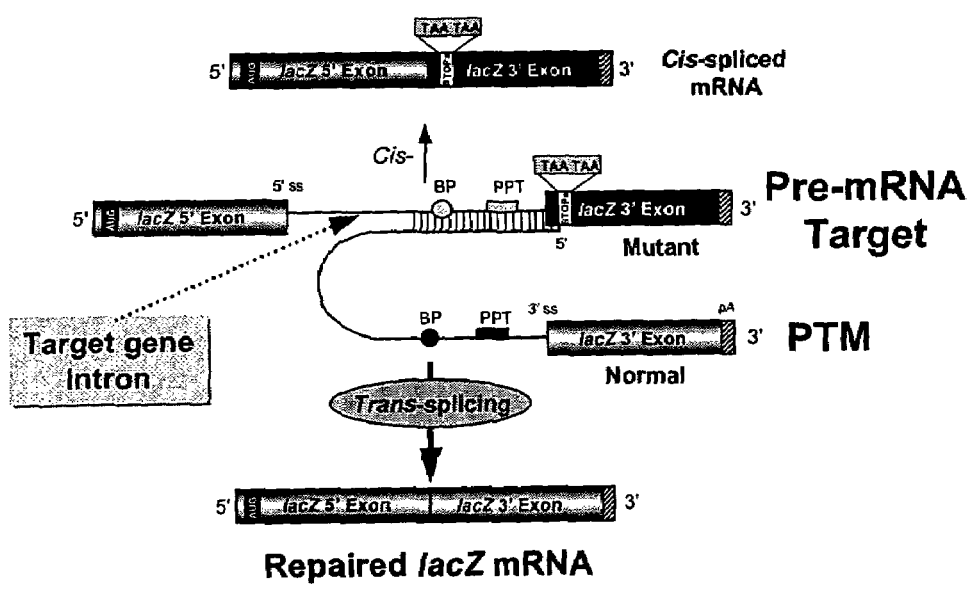
Figure 5B:
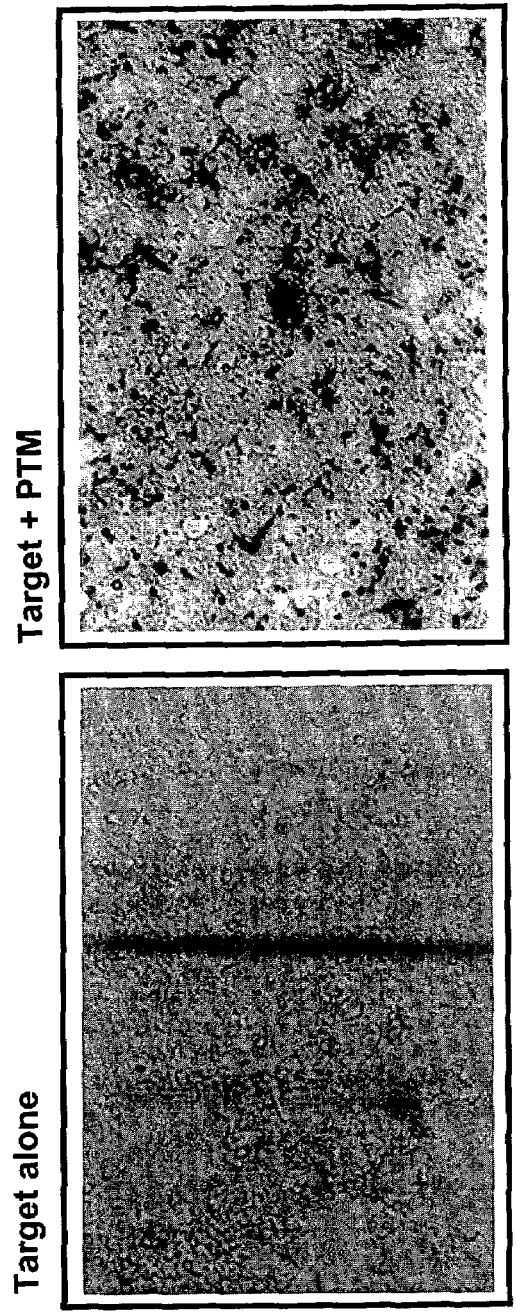

FIG. 5A. Trans-splicing mediated mRNA repair and production of functional protein. FIG. 5B. In situ staining for β-Gal activity following co-transfection in 293T cells (unselected). Cells transfected with (a) defective lacZ target alone, and (b) co-transfected with target and PTM.

Figure 6:
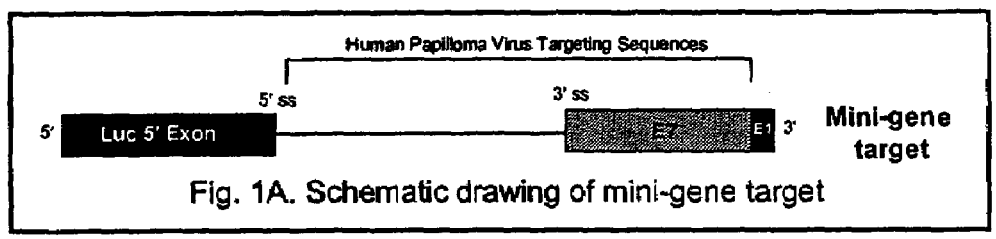

FIG. 6. Pre-mRNA target that is designed to express part of the synthetic Renilla luciferase sequence, coupled to the coding sequences for E7 and sequences immediately upstream of E7 from the human papilloma virus (HPV).

Figure 7:
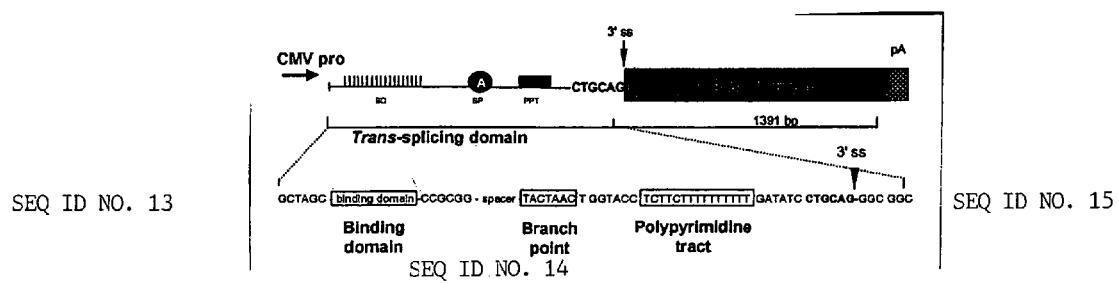

FIG. 7. Pre-trans-splicing molecule (PTM) designed to base pair with the target intron and trans-splice in the 3' luciferase "exon (SEQ ID NO:12)."

Figure 8:
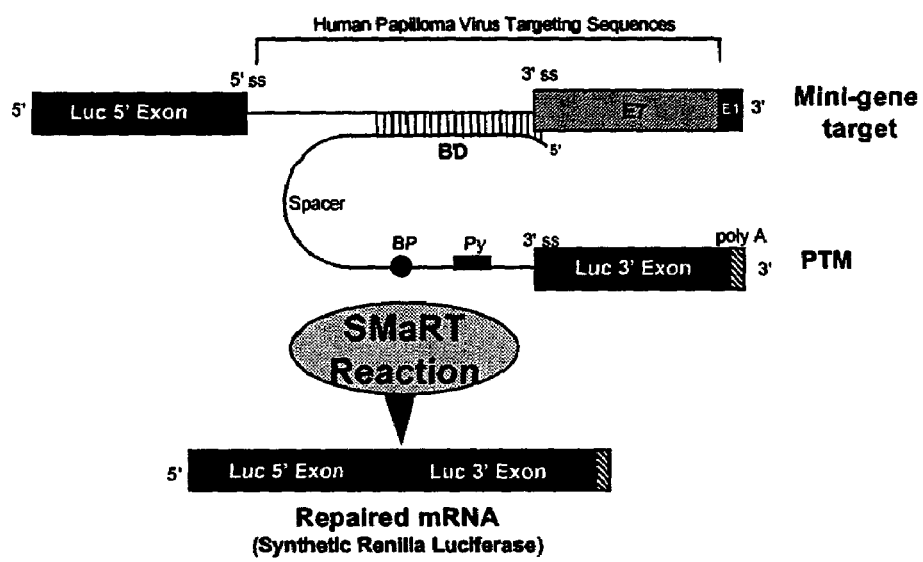

FIG. 8. Repair model showing the binding of PTM to the target pre-mRNA and restoration of luciferase activity by trans-splicing.

Figure 9:
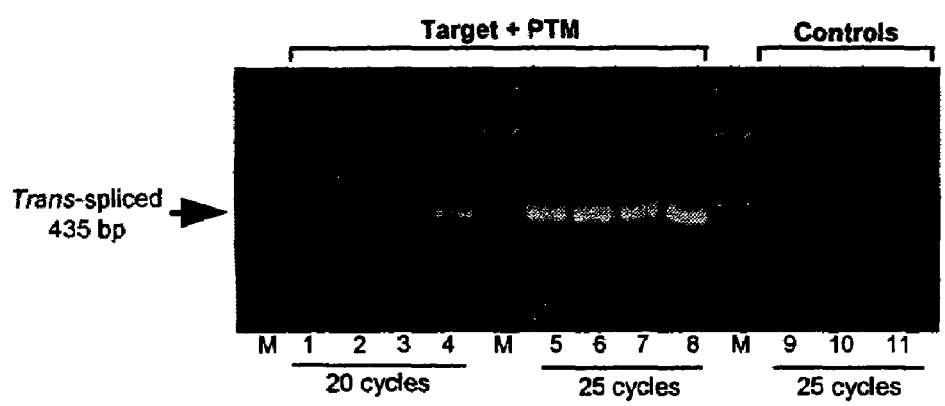

FIG. 9. RT-PCR analysis of total RNA using target and PTM specific primers that produced the expected trans-spliced (435 bp) product only in cells that contain both target and PTM but not in controls (target, PTM alone and target+splice mutant PTM).

Figure 10:
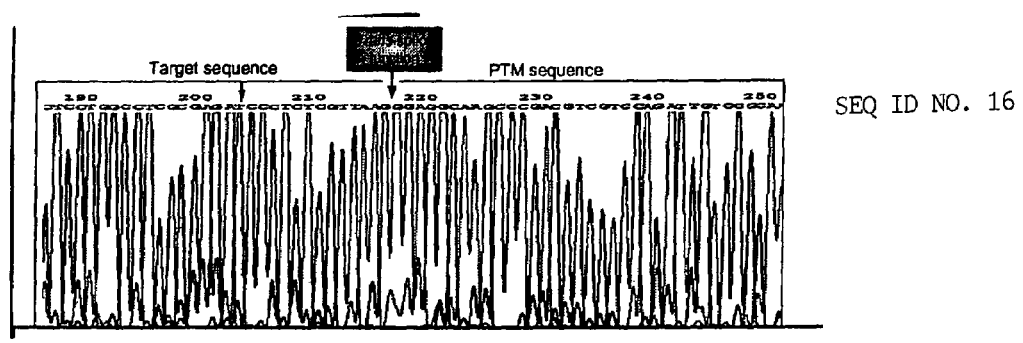

FIG. 10. Direct sequencing of the RT-PCR product confirms the accurate trans-splicing between the target and PTM (SEQ ID NO:16).

Figure 11:
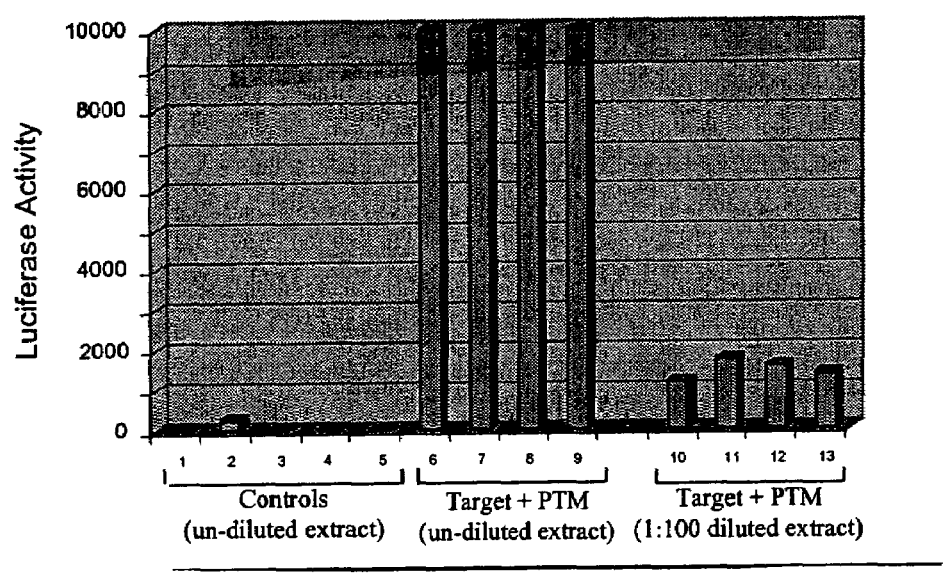

FIG. 11. Co-transfection of a specific target with Luc-PTM13 resulted in the repair and restoration of Renilla luciferase function that is on the order of 4-logs over background. No luciferase activity above background was detected in controls or with splice mutant PTMs suggesting that the restoration of luciferase function is due to trans-splicing.

Figure 12:
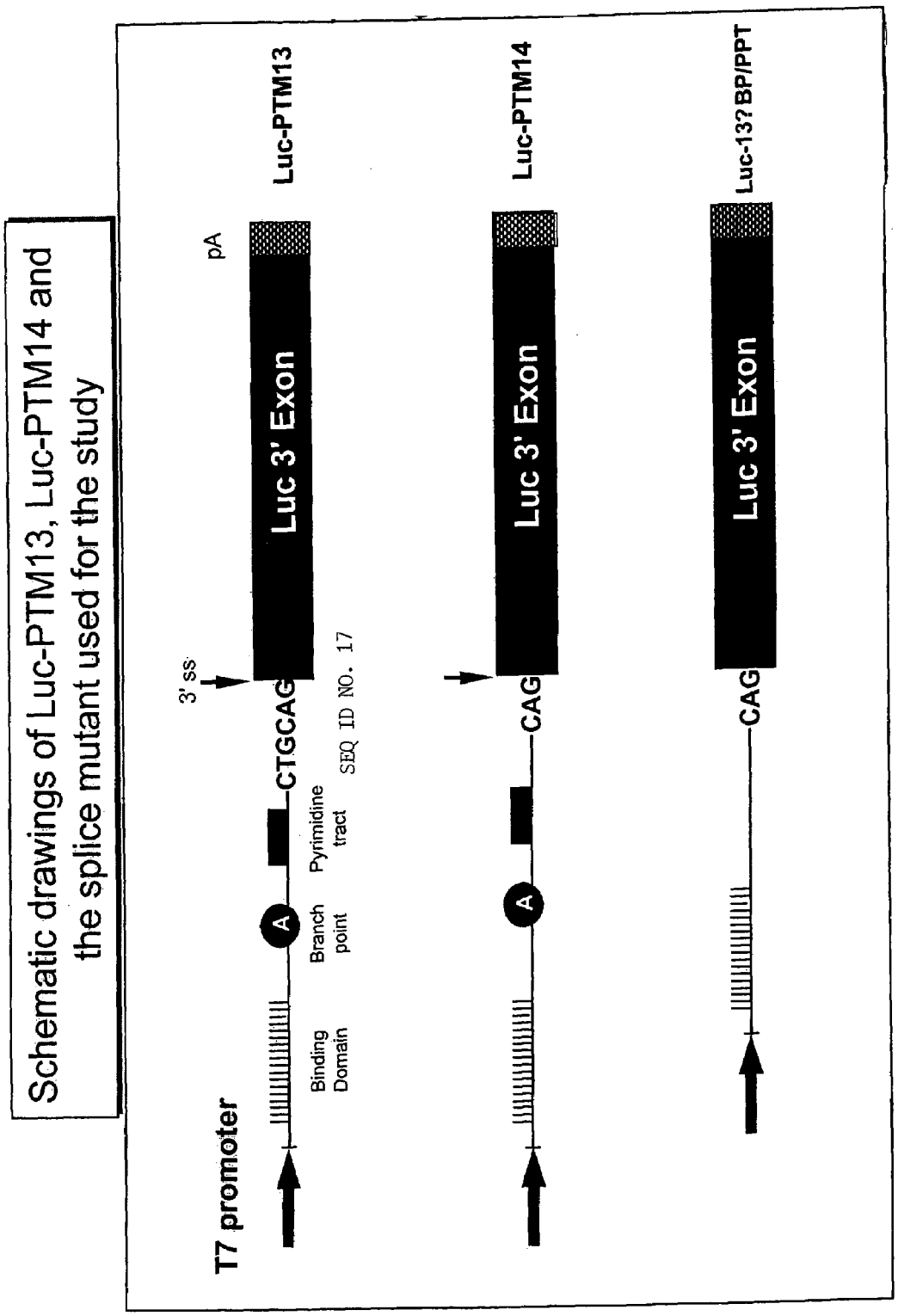

FIG. 12. Schematic drawings of Luc-PTM13, Luc-PTM14 and the splice mutant used for the study.

Figure 13:
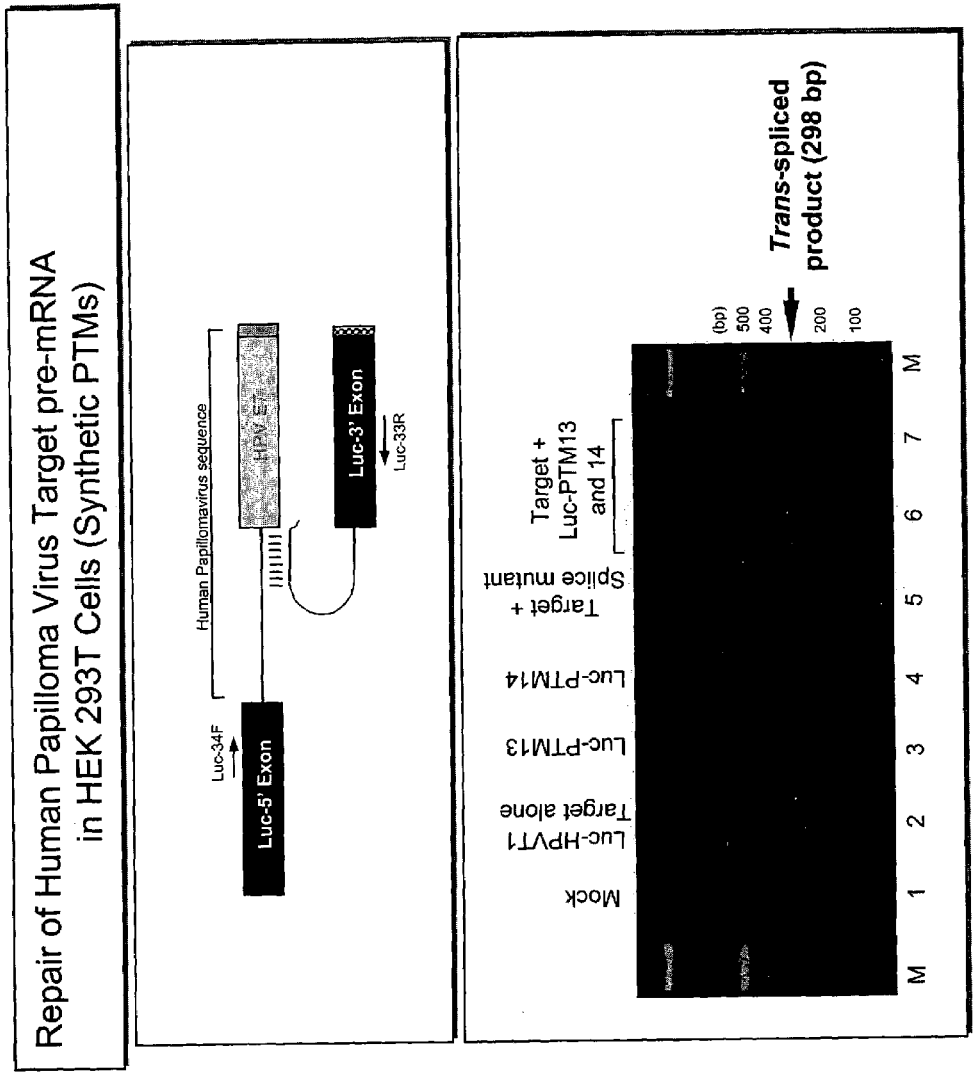

FIG. 13. Repair of human papilloma virus target pre-mRNA by trans-splicing in HEK293T cells.

Figure 14:
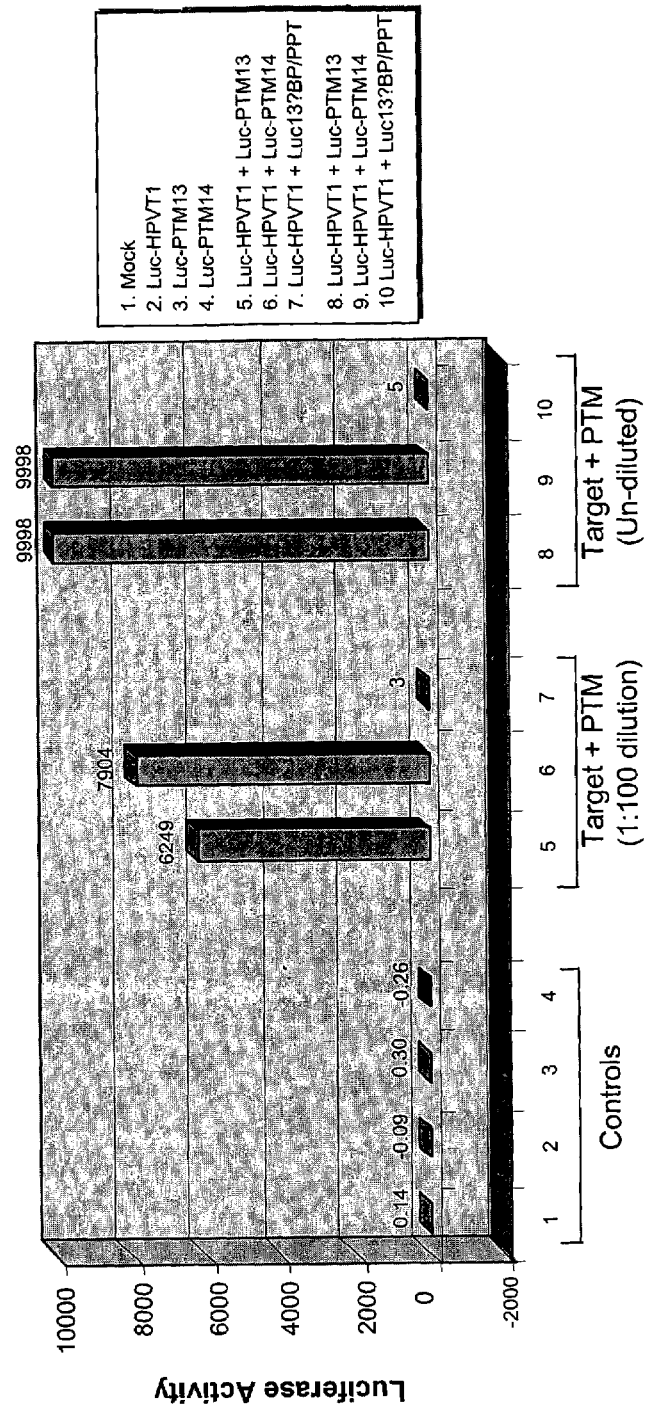

FIG. 14. Repair of human papilloma virus target pre-mRNA by trans-splicing and restoration of luciferase function in HEK293T cells.

Figure 15:
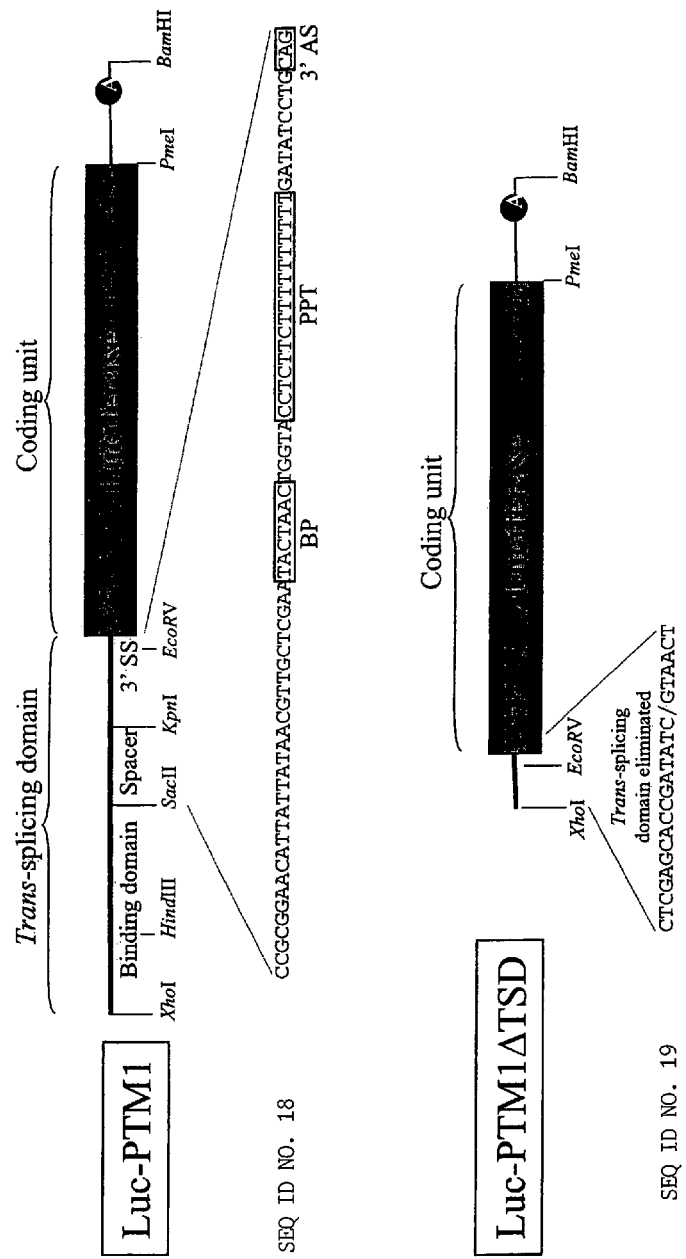

FIG. 15. Schematic of luciferase firefly pre-trans-splicing molecules (SEQ ID NO:18 and 19).

Figure 16:
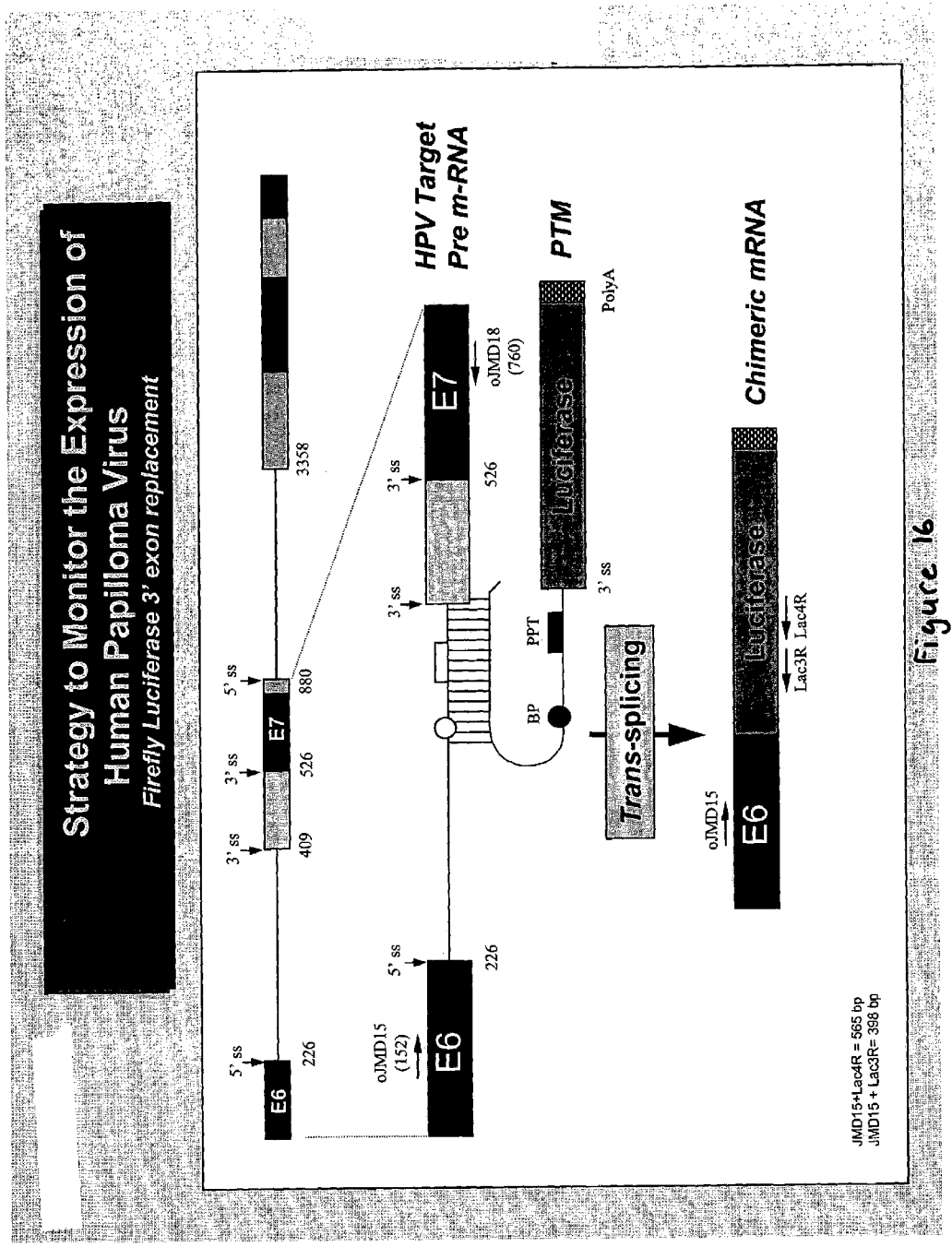

FIG. 16. Trans-splicing strategy to target the expression of human papilloma virus.

Figure 17:
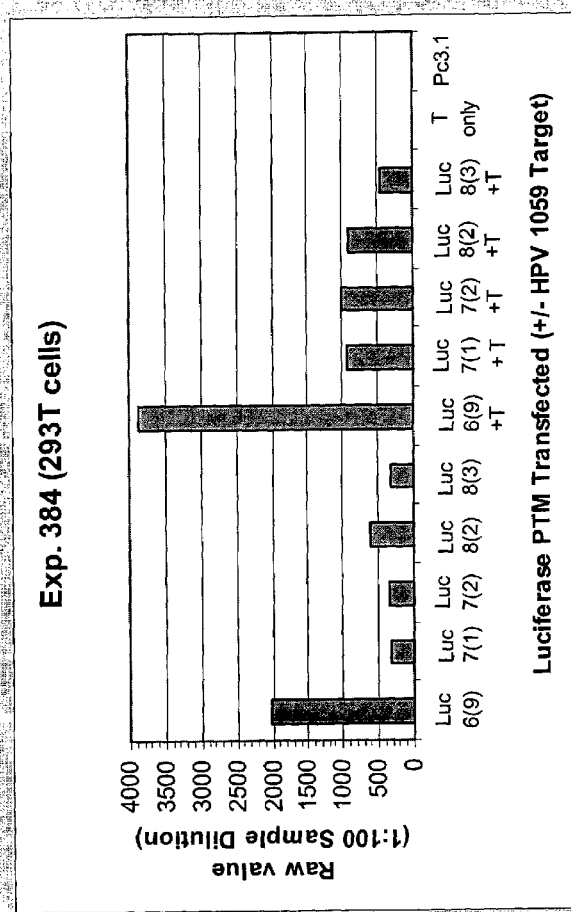

FIG. 17. Luciferase expression with and without target.

Figure 18:
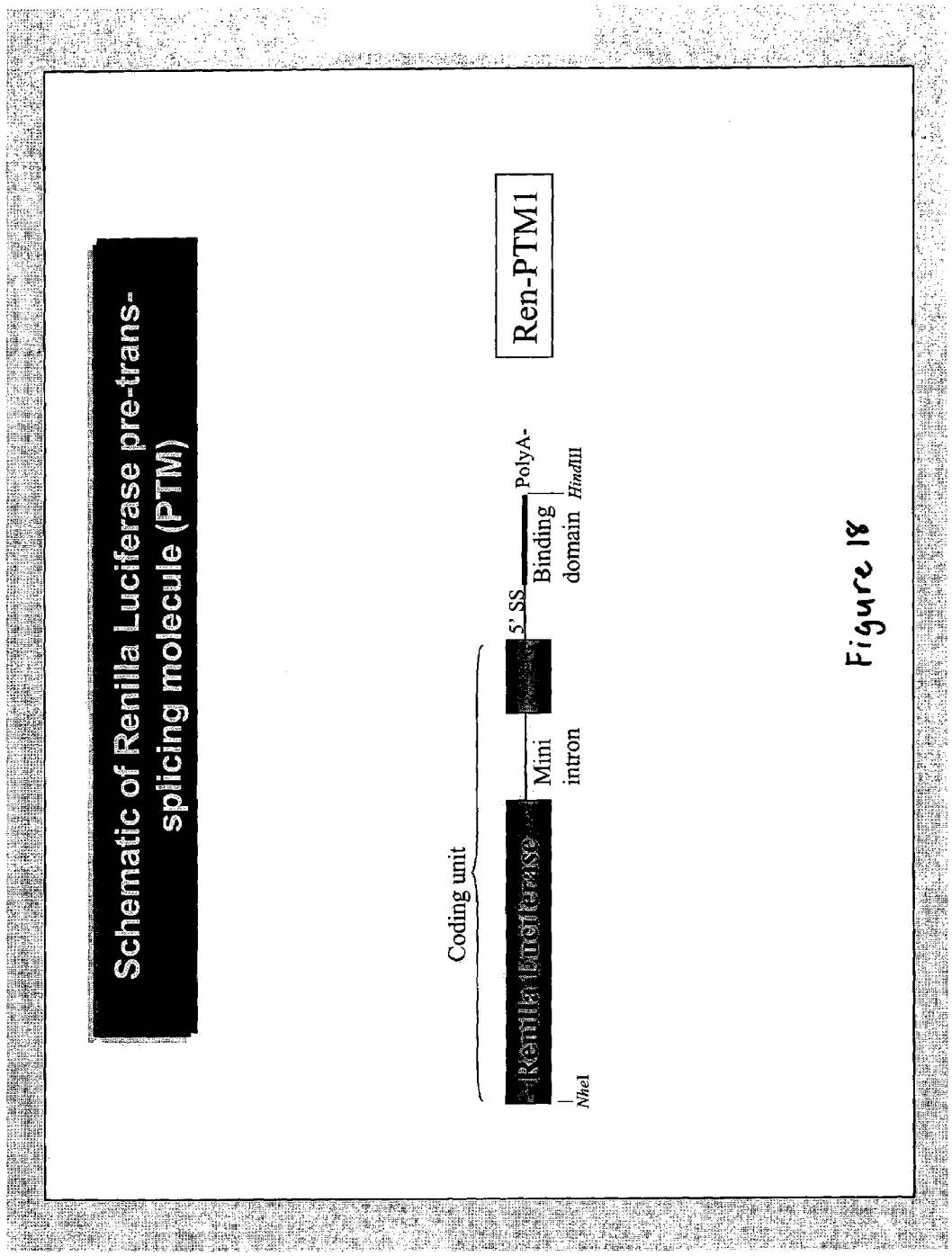

FIG. 18. Schematic of Renilla luciferase pre-trans-splicing molecule.

Figure 19:
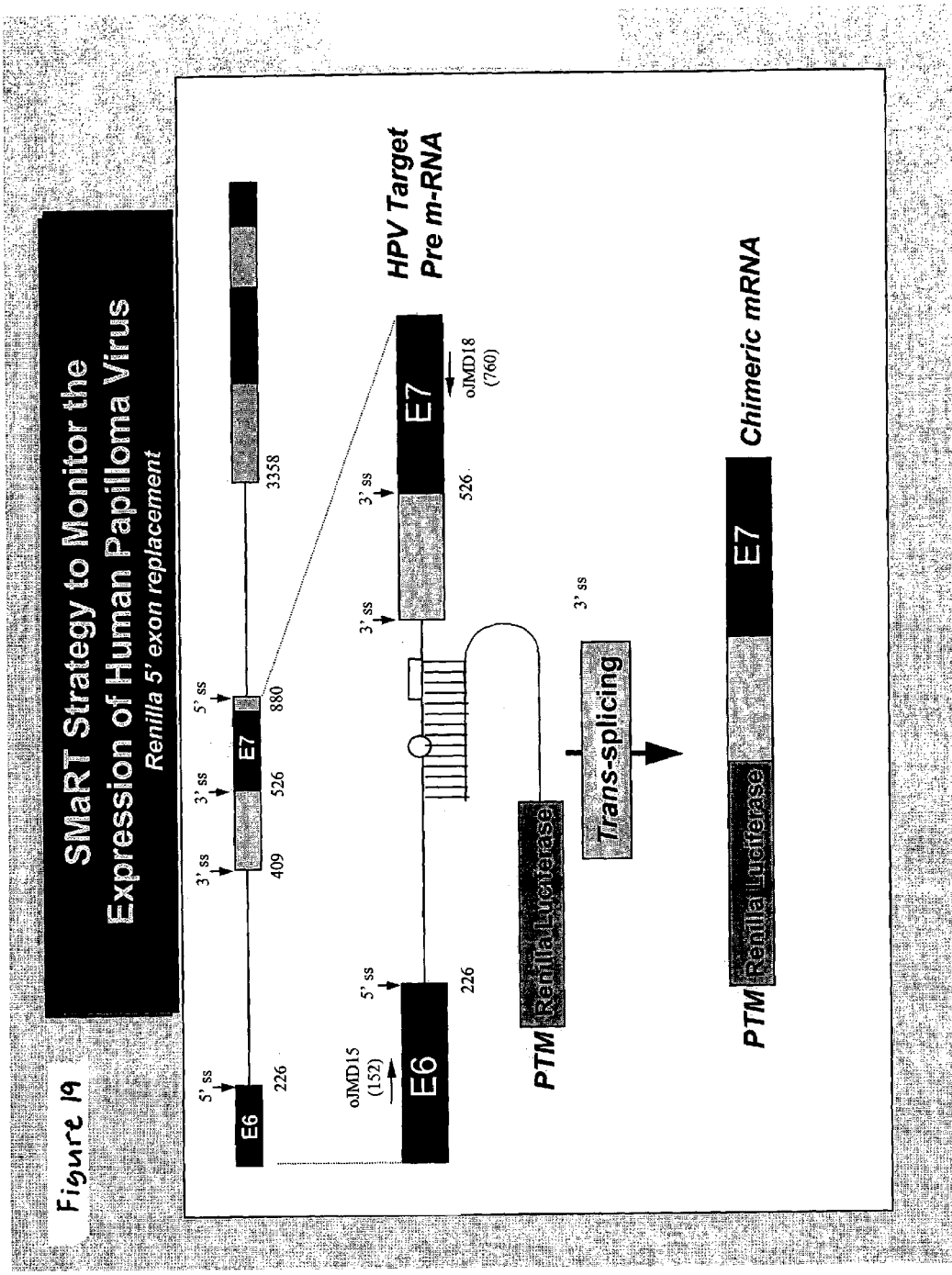

FIG. 19. Trans-splicing strategy to target the expression of human papilloma virus employs Renilla 5' "exon" replacement.

Figure 20:
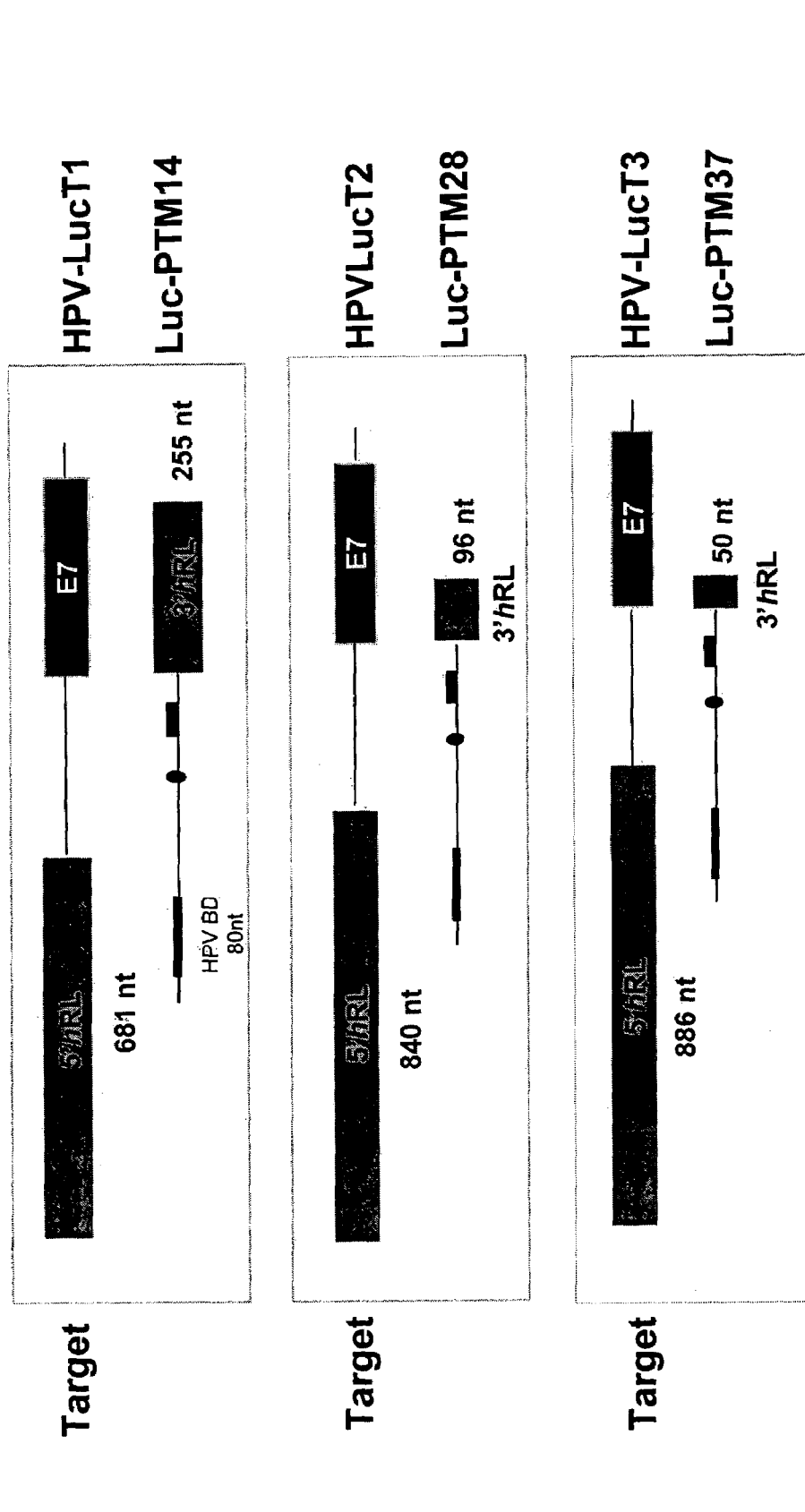

FIG. 20. Schematic diagrams of hemi-reporter model targets and PTMs used for targeting of gene expression. The mini-gene pre-mRNA targets consisting of 5' portion of humanized Renilla luciferase (hRluc) to act as a "5' exon" coupled to the E6-E7 intron region and adjacent E7 coding sequence of human papilloma virus (HPV16).

Figure 21:
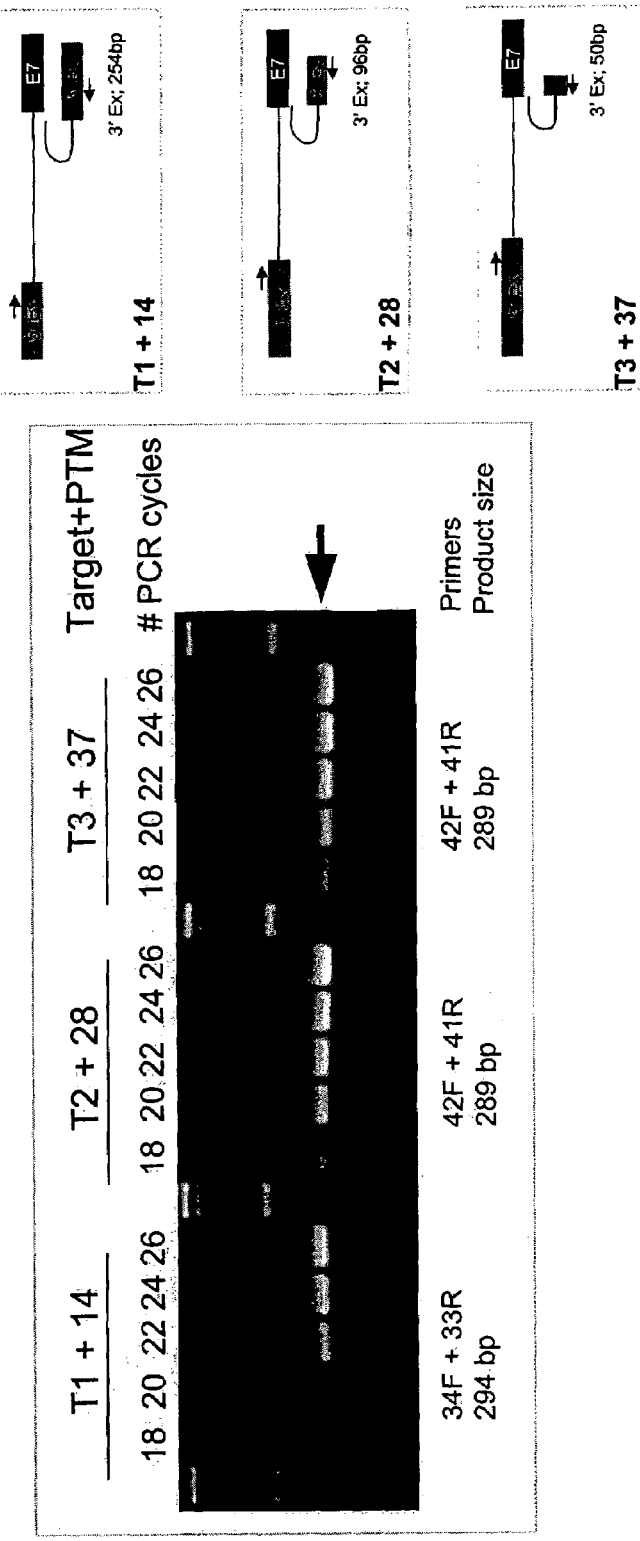

FIG. 21. Evaluation of trans-splicing efficiency at the RNA level.

Figure 22:
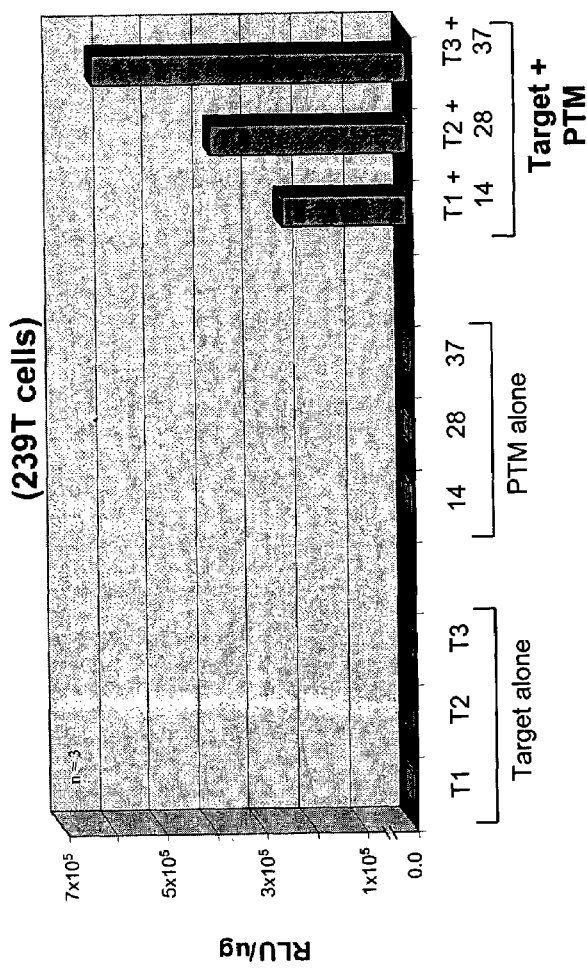

FIG. 22. Evaluation of trans-splicing efficiency at the functional level. The efficiency of trans-splicing mediated mRNA repair and restoration of Luciferase function was confirmed by assaying for enzymatic activity.

FIG. 23. In vivo expression of a light producing enzyme using trans-splicing. The full length PTM (Luc-PTM27) contains the complete coding sequence for humanized Renilla Luciferase (hRL) minus the AUG start codon. The trans-splicing domain consists of a strong 3' splice element (including a yeast consensus branch point (BP), a long pyrimidine tract (PPT) and a 3' acceptor site), a spacer sequence and a 80 nucleotide binding domain (BD) complementary to the 3' end of the intron between exons E6 and E7 of human papilloma virus (HPV-16) (FIG. 24A). Schematic illustration of trans-splicing mediated restoration of Luciferase function is shown in FIG. 24B.

Figure 24:
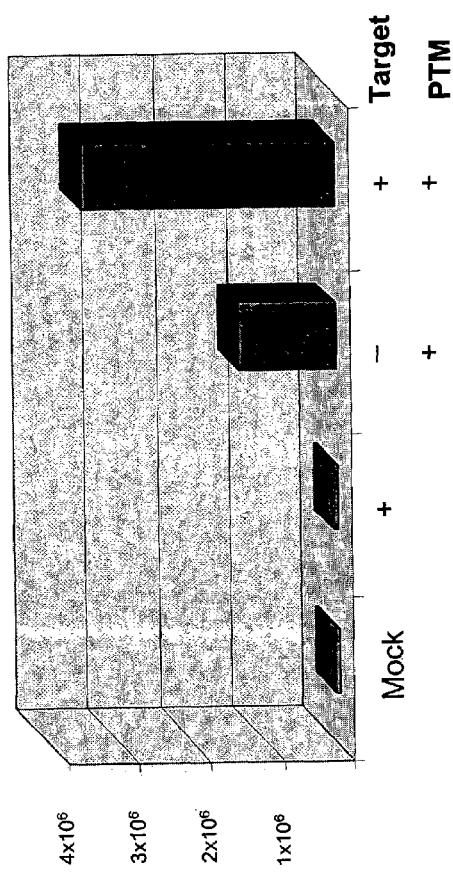

FIG. 24. Trans-splicing mediated mRNA repair and restoration of hRenilla Luciferase activity in 293T cells.

Figure 25A:
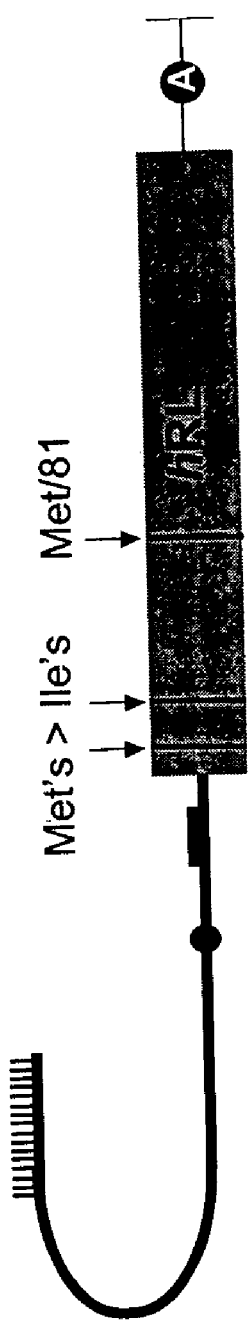
Figure 25B:
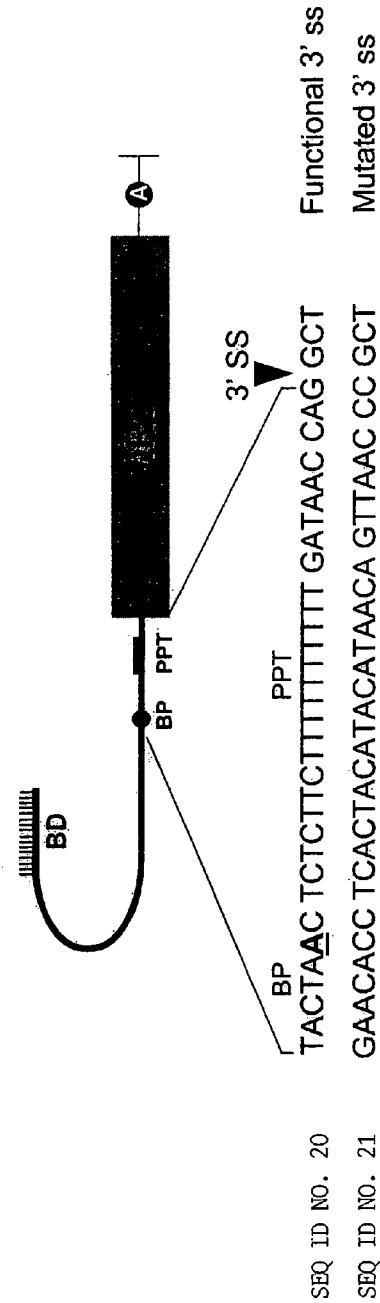

FIG. 25. Luciferase splice mutant PTM constructed to determine whether the restoration of Luciferase function is due to RNA trans-splicing. FIG. 25A, structure of a full-length PTM (functional PTM); FIG. 25B, structure of a splice-mutant PTM (SEQ ID NO:20 and 21). The splice mutant PTM is a derivative of Luc-PTM38 in which the 3' splice elements such as BP, PPT and the acceptor AG dinucleotide were modified by PCR mutagenesis and were confirmed by sequencing.

Figure 26:
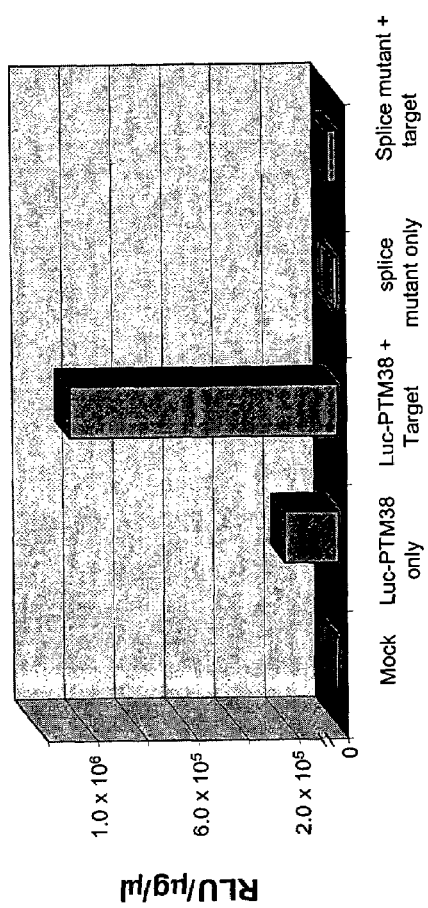

FIG. 26. Restoration of Luciferase function is due to RNA trans-splicing.

Figure 27:
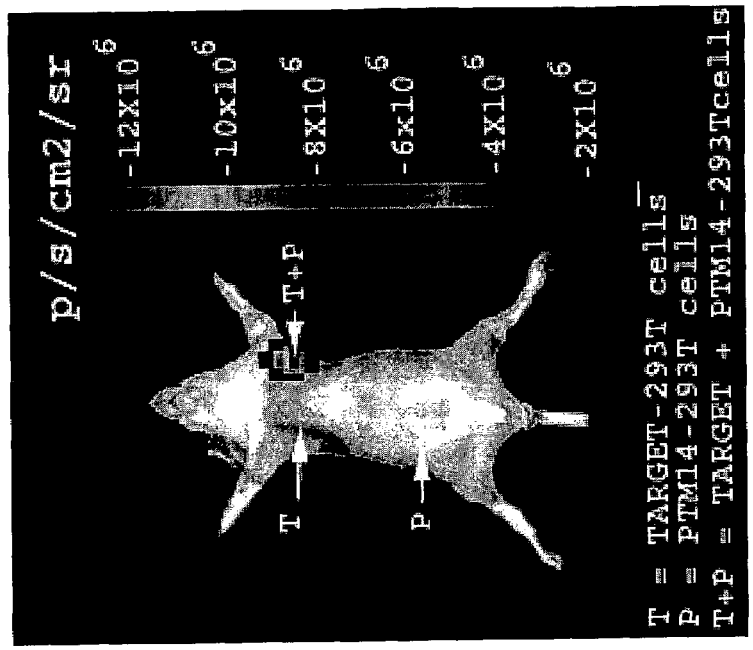
Figure 27:
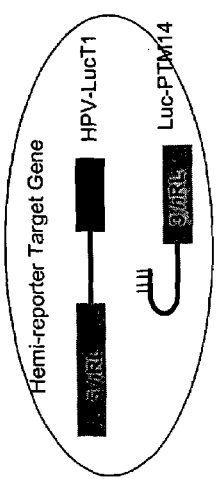

FIG. 27. In vivo expression of a light producing enzyme.

Figure 28:
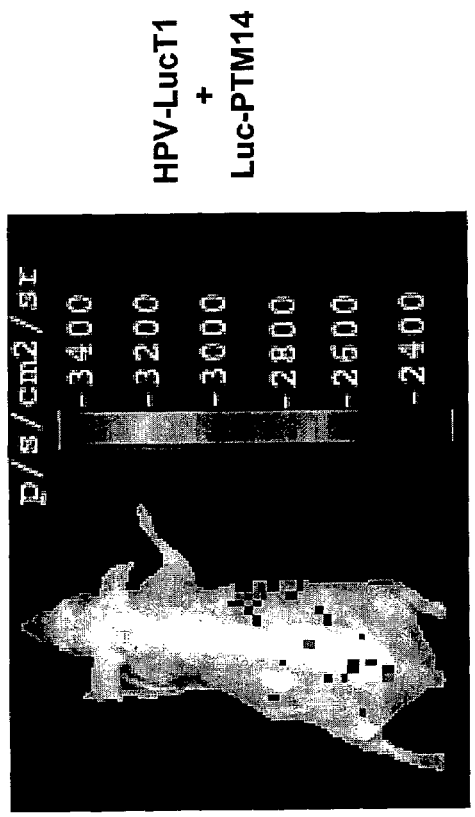

FIG. 28. In vivo expression of a light producing enzyme following IV PTM delivery.

5. DETAILED DESCRIPTION OF THE INVENTION

The present invention provides methods and compositions for conferring PTM mediated cell death on cells expressing a specific target precursor messenger RNA molecules. The target precursor messenger RNA molecules may be those selectively expressed in cancer cells, or alternatively, the RNA molecules may be those encoded by infectious agents such as bacteria, parasites, fungi or viruses. Target pre-mRNAs also include those cellular pre-mRNAs induced during or in response to bacterial, parasitic, fungal or viral infection, or, pre-mRNAs wherein expression of said pre-mRNA is associated with a specific disease or disorder. The compositions of the invention include pre-trans-splicing molecules (PTMs) designed to interact with one or more cancer cell selective target pre-mRNAs, or target pre-mRNAs encoded by an infectious agent, and mediate trans-splicing reactions resulting in the generation of a novel chimeric mRNA molecules (chimeric mRNA) encoding light producing proteins or enzymes capable of activating cytotoxic photosensitizers. Specifically, the PTMs of the invention are designed to encode light producing proteins or enzymes that are required for activation of photosensitizers which upon activation produce cytotoxic intermediates, including oxygen-related cytotoxic intermediates. The methods and compositions of the invention may be used to target expression of a light producing protein or enzyme to cancer cells or cells infected with a pathogenic agent thereby providing a method for selective destruction of cancer cells or cells infected with an infectious agent. Alternatively, the methods and compositions may be used to target cell death to a specific cell type based on the expression of cell-type specific mRNA.

5.1. Structure of the Pre-Trans-Splicing Molecules

The compositions of the invention include PTMs designed to interact with one or more selective target pre-mRNA molecule such as, for example, cancer cell selective target pre-mRNA, target pre-mRNA molecules encoded by an infectious agent, target cellular pre-mRNAs induced by an infectious microorganism, or target pre-mRNAs where the expression of said pre-mRNA is associated with a disease or disorder. Such RNAs are designed to mediate trans-splicing reactions resulting in the generation of novel chimeric mRNA molecules (chimeric mRNAs). The novel chimeric mRNA is designed to encode a light producing protein or enzyme capable of activating a cytotoxic photosensitizer. Such activation leads to cell death. The compositions of the invention provide a means for conferring selective death on cells expressing a specific target pre-mRNA. The PTMs comprising (i) one or more target binding domains that targets binding of the PTM to a specific pre-mRNA target (ii) a 3' splice region that includes a 3' splice acceptor site and/or 5' splice donor site; and (iii) a nucleotide sequence capable of encoding a light producing protein or enzyme.

In some instances, the PTMs of the invention may further comprise one or more spacer regions that separate the RNA splice site from the target binding domains and/or a safety sequence. The structure of PTMs is described in detail in U.S. Pat. Nos. 6,013,487, 6,083,702, 6,280,978, and in co-pending U.S. patent application Ser. Nos. 09/756,095, 09/756,096, 09/756,097 the disclosures of which are incorporated by reference herein.

The target-binding domain of the PTM may contain multiple binding domains which are complementary to and in anti-sense orientation to the targeted region of the target specific pre-mRNA, e.g., a cancer selective pre-mRNA or a pre-mRNA encoded by a pathogenic microorganism. As used herein, a target binding domain(s) is defined as any sequence that confers specificity of binding and anchors the pre-mRNA closely in space so that the spliceosome processing machinery of the nucleus can trans-splice a portion of the PTM to a portion of the pre-mRNA. The target binding domains may comprise up to several thousand nucleotides. In preferred embodiments of the invention the binding domains may comprise at least 10 to 30 and up to several hundred nucleotides. The specificity of the PTM may be increased significantly by increasing the length of the target binding domain. In addition, although the target binding domain may be "linear" it is understood that the RNA may fold to form secondary structures that may stabilize the complex by preventing activation of the PTM splice site until the binding domain has encountered its target thereby increasing the efficiency of splicing. Absolute complementarity with the targeted cell selective pre-mRNA, although preferred, is not required. A sequence "complementary" to a portion of an RNA, as referred to herein, means a sequence having sufficient complementarity to be able to hybridize with the RNA, forming a stable duplex. The ability to hybridize will depend on both the degree of complementarity and the length of the nucleic acid (See, for example, Sambrook et al., 1989, Molecular Cloning, A Laboratory Manual, 2d Ed., Cold Spring Harbor Laboratory Press, Cold Spring Harbor, N.Y.). Generally, the longer the hybridizing nucleic acid, the more base mismatches with an RNA it may contain and still form a stable duplex. One skilled in the art can ascertain a tolerable degree of mismatch or length of duplex by use of standard procedures to determine the stability of the hybridized complex.

In an embodiment of the invention, the target binding domain of the PTM will contain sequences which are complementary to and in anti-sense orientation to a cancer cell selective target pre-mRNA molecules where the goal is to target expression of a light producing protein or enzyme to cancer cells thereby targeting cancer cell destruction. For example, PTM binding sites may be engineered to bind to any target pre-mRNA where the expression of the target pre-mRNA is associated with a proliferative disorder or disease. Such target pre-mRNAs are characterized as those pre-mRNAs expressed in cancer cells but which are either absent or expressed in low levels in their normal cell counterparts. Such target pre-mRNAs include, for example, the β-chorionic gonadotropin 6 pre-mRNA, the epidermal growth factor receptor pre-mRNA, E2F-1 pre mRNA or telomerase pre mRNA each of which are known to be over expressed in tumor cells and prostate specific G-protein coupled receptor (PSGR) pre-mRNA which is known to be over expressed in prostate cancer.

The methods and compositions of the present invention may be designed to target any pre-mRNA known to be differentially expressed in cancer cells but not normal cells. Additionally, techniques well known to those of skill in the art may be used to identify novel genes differentially expressed in cancer cells but not their normal counterpart. Such techniques includes, for example, the use of cDNA microarrays to identify differentially expressed genes in cancer cells. (See, Ausebel et al., 2003, Current Protocols in Molecular Biology, John Wiley & Sons, Inc., Chapter 25)

In yet another embodiment of the invention, the target binding domain of the PTM will contain sequences which are complementary to and in anti-sense orientation to specific target pre-mRNA molecules encoded by an infectious agent where the goal is to target expression of a light producing protein or enzyme to cells infected with the agent thereby targeting infected cell destruction. For example, PTM binding sites may be engineered to bind to any target pre-mRNA where the expression of the target pre-mRNA is associated with a viral, bacterial, fungal or parasitic disease, for example.

Binding may also be achieved through other mechanisms, for example, through triple helix formation or protein/nucleic acid interactions such as those in which the PTM is engineered to recognize a specific RNA binding protein, e.g., a protein bound to a specific target pre-mRNA. Alternatively, the PTMs of the invention may be designed to recognize secondary structures, such as for example, hairpin structures resulting from intramolecular base pairing between nucleotides within an RNA molecule.

As indicated above, the PTM molecules of the invention are also designed to contain a 3' splice region that may include a branchpoint, pyrimidine tract and a 3' splice acceptor AG site and/or a 5' splice donor site. Consensus sequences for the 5' splice donor site and the 3' splice region used in RNA splicing are well known in the art (See, Moore, et al., 1993, The RNA World, Cold Spring Harbor Laboratory Press, p. 303-358). In addition, modified consensus sequences that maintain the ability to function as 5' donor splice sites and 3' splice regions may be used in the practice of the invention. Briefly, the 5' splice site consensus sequence is AG/GURAGU (SEQ ID NO. 1) (where A=adenosine, U=uracil, G=guanine, C=cytosine, R=purine and/=the splice site). The 3' splice site consists of three separate sequence elements: the branchpoint or branch site, a polypyrimidine tract and the 3' consensus sequence (YAG). The branchpoint consensus sequence in mammals is YNYURAC (SEQ ID NO. 2) (Y=pyrimidine). The underlined A is the site of branch formation. A polypyrimidine tract is located between the branchpoint and the splice site acceptor and is important for efficient branchpoint utilization and 3' splice site recognition.

Recently, pre-messenger RNA introns beginning with the dinucleotide AU and ending with the dinucleotide AC have been identified and referred to as U12 introns. U12 intron sequences as well as any sequences that function as splice acceptor/donor sequences may also be used in PTMs.

A spacer region to separate the RNA splice site from the target binding domain may also be included in the PTM. The spacer region may have additional features such as sequences that enhance trans-splicing to the target pre-mRNA. In a specific embodiment of the invention, initiation codon(s) and pre-mature termination codons may be incorporated into the PTMs of the invention as a mechanism for targeting selective degradation of unspliced RNAs thereby preventing translation and expression of unspliced RNAs from the nucleus into the cytoplasm. (see, Kim et al., 2001 Science 293:1832-1836)

In a preferred embodiment of the invention, a "safety" is also incorporated into the spacer, binding domain, or elsewhere in the PTM to prevent non-specific trans-splicing. This is a region of the PTM that covers elements of the 3' and/or 5' splice site of the PTM by relatively weak complementarity, preventing non-specific trans-splicing. The PTM is designed in such a way that upon hybridization of the binding/targeting portion(s) of the PTM, the 3' and/or 5' splice site is uncovered and becomes fully active.

The "safety" consists of one or more complementary stretches of cis-sequence (or could be a second, separate, strand of nucleic acid) which weakly binds to one or both sides of the PTM branchpoint, pyrimidine tract, 3' splice site and/or 5' splice site (splicing elements), or could bind to parts of the splicing elements themselves. This "safety" binding prevents the splicing elements from being active (e.g., block U2 snRNP, U1, or other splicing factors from attaching to the PTM splice site recognition elements). The binding of the "safety" may be disrupted by the binding of the target binding region of the PTM to the target pre-mRNA, thus exposing and activating the PTM splicing elements (making them available to trans-splice into the target pre-mRNA).

A nucleotide sequence encoding a translatable protein capable of producing a light producing enzyme or protein is included in the PTM of the invention. Such enzymes are capable of producing light in the presence of substrate. Such proteins include but are not limited to bioluminescent and fluorescent molecules. Bioluminescent molecules include but are not limited to firefly, Renilla or bacterial luciferase. Fluorescent molecules include, for example, green fluorescent protein or red fluorescent protein. FIG. 3 is a representation of a prototype PTM designed to express a luciferase light producing enzyme. FIG. 4 illustrates a PTM encoding luciferase including a safety mechanism.

Additional features can be added to the PTM molecule either after, or before, the nucleotide sequence encoding the light producing enzyme. Such features include polyadenylation signals, 5' splice sequences capable of enhancing splicing, additional binding regions or additional splice sites. Stop codons or other elements in the region between the binding domain and the splice site may be added to prevent unspliced pre-mRNA expression. In another embodiment of the invention, PTMs can be generated with a second anti-sense binding domain downstream from the nucleotide sequences encoding a translatable protein to promote binding to the 3' target intron or exon and to block the fixed authentic cis-5' splice site (U5 and/or U1 binding sites). Further elements such as a 3' hairpin structure, circularized RNA, sequences that promote or facilitate nuclear localization and spliceosomal incorporation, and stability may be incorporated.

Sequences referred to as exonic splicing enhancers may also be included in the structure of the synthetic PTMs. Trans-acting splicing factors, namely the serine/arginine-rich (SR) proteins, have been shown to interact with such exonic splicing enhancers and modulate splicing (See, Tacke et al., 1999, Curr. Opin. Cell Biol. 11:358-362; Tian et al., 2001, J. Biological Chemistry 276:33833-33839; Fu, 1995, RNA 1:663-680). Nuclear localization signals may also be included in the PTM molecule (Dingwell and Laskey, 1986, Ann. Rev. Cell Biol. 2:367-390; Dingwell and Laskey, 1991, Trends in Biochem. Sci. 16:478-481). Such nuclear localization signals can be used to enhance the transport of synthetic PTMs into the nucleus where trans-splicing occurs. In addition, sequences may be used that enhance the retention of PTMs in the nucleus (Boelans et al., 1995 RNA 1:273-83; Good et al., 1997 Gene Ther. 4:45-54).

When using synthetic PTMs, the PTMs of the invention can be modified at the base moiety, sugar moiety, or phosphate backbone, for example, to improve stability of the molecule, hybridization to the target mRNA, transport into the cell, etc. For example, modification of a PTM to reduce the overall charge can enhance the cellular uptake of the molecule. In addition modifications can be made to reduce susceptibility to nuclease or chemical degradation. The nucleic acid molecules may be synthesized in such a way as to be conjugated to another molecule such as a peptides (e.g., for targeting host cell receptors in vivo), or an agent facilitating transport across the cell membrane (see, e.g., Letsinger et al., 1989, Proc. Natl. Acad. Sci. USA 86:6553-6556; Lemaitre et al., 1987, Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, BioTechniques 6:958-976) or intercalating agents (see, e.g., Zon, 1988, Pharm. Res. 5:539-549). To this end, the nucleic acid molecules may be conjugated to another molecule, e.g., a peptide, hybridization triggered cross-linking agent, transport agent, hybridization-triggered cleavage agent, etc.

Various other well-known modifications to the nucleic acid molecules can be introduced as a means of increasing stability and half-life. Possible modifications include, but are not limited to, the addition of flanking sequences of ribonucleotides to the 5' and/or 3' ends of the molecule. In some circumstances where increased stability is desired, nucleic acids having modified internucleoside linkages such as 2'-0-methylation may be preferred. Nucleic acids containing modified internucleoside linkages may be synthesized using reagents and methods that are well known in the art (see, Uhlmann et al., 1990, Chem. Rev. 90:543-584; Schneider et al., 1990, Tetrahedron Lett. 31:335 and references cited therein).

Synthetic PTMs of the present invention are preferably modified in such a way as to increase their stability. Since RNA molecules are sensitive to cleavage by cellular ribonucleases, it may be preferable to use as the competitive inhibitor a chemically modified oligonucleotide (or combination of oligonucleotides) that mimics the action of the RNA binding sequence but is less sensitive to nuclease degradation. In addition, the synthetic PTMs can be produced as nuclease resistant circular molecules with enhanced stability (Puttaraju et al., 1995, Nucleic Acids Symposium Series No. 33:49-51; Puttaraju et al., 1993, Nucleic Acid Research 21:4253-4258). Other modifications may also be required, for example to enhance binding, to enhance cellular uptake, to improve pharmacology or pharmacokinetics or to improve other pharmaceutically desirable characteristics.

Modifications, which may be made to the structure of the synthetic PTMs include but are not limited to backbone modifications such as use of: (i) phosphorothioates (X or Y or W or Z=S or any combination of two or more with the remainder as O). e.g. Y=S (Stein, C. A., et al., 1988, Nucleic Acids Res., 16:3209-3221), X=S (Cosstick, R., et al., 1989, Tetrahedron Letters, 30, 4693-4696), Y and Z=S (Brill, W. K.-D., et al., 1989, J. Amer. Chem. Soc., 111:2321-2322); (ii) methylphosphonates (e.g. Z=methyl (Miller, P. S., et al., 1980, J. Biol. Chem., 255:9659-9665); (iii) phosphoramidates (Z=N-(alkyl)2 e.g. alkyl methyl, ethyl, butyl) (Z=morpholine or piperazine) (Agrawal, S., et al., 1988, Proc. Natl. Acad. Sci. USA 85:7079-7083) (X or W=NH) (Mag, M., et al., 1988, Nucleic Acids Res., 16:3525-3543); (iv) phosphotriesters (Z=O-alkyl e.g. methyl, ethyl, etc) (Miller, P. S., et al., 1982, Biochemistry, 21:5468-5474); and (v) phosphorus-free linkages (e.g. carbamate, acetamidate, acetate) (Gait, M. J., et al., 1974, J. Chem. Soc. Perkin I, 1684-1686; Gait, M. J., et al., 1979, J. Chem. Soc. Perkin I, 1389-1394). See also, Sazani et al., 1974, Nucleic Acids Research 29:3965-3974.

In addition, sugar modifications may be incorporated into the PTMs of the invention. Such modifications include but are not limited to the use of: (i) 2'-ribonucleosides (R=H); (ii) 2'-O-methylated nucleosides (R=OMe) (Sproat, B. S., et al., 1989, Nucleic Acids Res., 17:3373-3386); and (iii) 2'-fluoro-2'-ribonucleosides (R=F) (Krug, A., et al., 1989, Nucleosides and Nucleotides, 8:1473-1483).

Further, base modifications that may be made to the PTMs, including but not limited to use of: (i) pyrimidine derivatives substituted in the 5-position (e.g. methyl, bromo, fluoro etc) or replacing a carbonyl group by an amino group (Piccirilli, J. A., et al., 1990, Nature, 343:33-37); (ii) purine derivatives lacking specific nitrogen atoms (e.g. 7-deaza adenine, hypoxanthine) or functionalized in the 8-position (e.g. 8-azido adenine, 8-bromo adenine) (for a review see Jones, A. S., 1979, Int. J. Biolog. Macromolecules, 1:194-207).

In addition, the PTMs may be covalently linked to reactive functional groups, such as: (i) psoralens (Miller, P. S., et al., 1988, Nucleic Acids Res., Special Pub. No. 20, 113-114), phenanthrolines (Sun, J-S., et al., 1988, Biochemistry, 27:6039-6045), mustards (Vlassov, V. V., et al., 1988, Gene, 72:313-322) (irreversible cross-linking agents with or without the need for co-reagents); (ii) acridine (intercalating agents) (Helene, C., et al., 1985, Biochimie, 67:777-783); (iii) thiol derivatives (reversible disulphide formation with proteins) (Connolly, B. A., and Newman, P. C., 1989, Nucleic Acids Res., 17:4957-4974); (iv) aldehydes (Schiff's base formation); (v) azido, bromo groups (UV cross-linking); or (vi) ellipticines (photolytic cross-linking) (Perrouault, L., et al., 1990, Nature, 344:358-360).

In an embodiment of the invention, oligonucleotide mimetics in which the sugar and internucleoside linkage, i.e., the backbone of the nucleotide units, are replaced with novel groups can be used. For example, one such oligonucleotide mimetic which has been shown to bind with a higher affinity to DNA and RNA than natural oligonucleotides is referred to as a peptide nucleic acid (PNA) (for review see, Uhlmann, E. 1998, Biol. Chem. 379:1045-52). Thus, PNA may be incorporated into synthetic PTMs to increase their stability and/or binding affinity for the target pre-mRNA.

In another embodiment of the invention synthetic PTMs may covalently linked to lipophilic groups or other reagents capable of improving uptake by cells. For example, the PTM molecules may be covalently linked to: (i) cholesterol (Letsinger, R. L., et al., 1989, Proc. Natl. Acad. Sci. USA, 86:6553-6556); (ii) polyamines (Lemaitre, M., et al., 1987, Proc. Natl. Acad. Sci, USA, 84:648-652); other soluble polymers (e.g. polyethylene glycol) to improve the efficiently with which the PTMs are delivered to a cell. In addition, combinations of the above identified modifications may be utilized to increase the stability and delivery of PTMs into the target cell.

5.2. Synthesis of the Trans-Splicing Molecules

The nucleic acid molecules of the invention can be RNA or DNA or derivatives or modified versions thereof, single-stranded or double-stranded. By nucleic acid is meant a PTM molecule or a nucleic acid molecule encoding a PTM molecule, whether composed of deoxyribonucleotides or ribonucleotides, and whether composed of phosphodiester linkages or modified linkages. The term nucleic acid also specifically includes nucleic acids composed of bases other than the five biologically occurring bases (adenine, guanine, thymine, cytosine and uracil).

The RNA and DNA molecules of the invention can be prepared by any method known in the art for the synthesis of DNA and RNA molecules. For example, the nucleic acids may be chemically synthesized using commercially available reagents and synthesizers by methods that are well known in the art (Gait, 1985, Oligonucleotide Synthesis: A Practical Approach, IRL Press, Oxford, England). Alternatively, RNA molecules can be generated by in vitro and in vivo transcription of DNA sequences encoding the RNA molecule. Such DNA sequences can be incorporated into a wide variety of vectors which incorporate suitable RNA polymerase promoters such as the T7 or SP6 polymerase. RNAs may be produced in high yield via in vitro transcription using plasmids such as SPS65 (Promega Corporation, Madison, Wis.). In addition, RNA amplification methods such as Q-β amplification can be utilized to produce RNAs.

The nucleic acid molecules can be modified at the base moiety, sugar moiety, or phosphate backbone, for example, to improve stability of the molecule, hybridization, transport into the cell, etc. For example, modification of a PTM to reduce the overall charge can enhance the cellular uptake of the molecule. In addition modifications can be made to reduce susceptibility to nuclease degradation. The nucleic acid molecules may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. W088/09810, published Dec. 15, 1988) or the blood-brain barrier (see, e.g., PCT Publication No. W089/10134, published Apr. 25, 1988), hybridization-triggered cleavage agents. (See, e.g., Krol et al., 1988, Bio-Techniques 6:958-976) or intercalating agents. (See, e.g., Zon, 1988, Pharm. Res. 5:539-549). To this end, the nucleic acid molecules may be conjugated to another molecule, e.g., a peptide, hybridization triggered cross-linking agent, transport agent, hybridization-triggered cleavage agent, etc. Various other well-known modifications to the nucleic acid molecules can be introduced as a means of increasing intracellular stability and half-life. Possible modifications include, but are not limited to, the addition of flanking sequences of ribo- or deoxy-nucleotides to the 5' and/or 3' ends of the molecule. In some circumstances where increased stability is desired, nucleic acids having modified internucleoside linkages such as 2'-0-methylation may be preferred. Nucleic acids containing modified internucleoside linkages may be synthesized using reagents and methods that are well known in the art (see, Uhlmann et al., 1990, Chem. Rev. 90:543-584; Schneider et al., 1990, Tetrahedron Lett. 31:335 and references sited therein).

The nucleic acids may be purified by any suitable means, as are well known in the art. For example, the nucleic acids can be purified by reverse phase chromatography or gel electrophoresis. Of course, the skilled artisan will recognize that the method of purification will depend in part on the size and charge of the nucleic acid to be purified.

In instances where a nucleic acid molecule encoding a PTM is utilized, cloning techniques known in the art may be used for cloning of the nucleic acid molecule into an expression vector. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

The DNA encoding the PTM of interest may be recombinantly engineered into a variety of host vector systems that also provide for replication of the DNA in large scale and contain the necessary elements for directing the transcription of the PTM. The use of such a construct to transfect target cells in the patient will result in the transcription of sufficient amounts of PTMs that will form complementary base pairs with the endogenously expressed pre-mRNA targets and thereby facilitate a trans-splicing reaction between the complexed nucleic acid molecules. For example, a vector can be introduced in vivo such that it is taken up by a cell and directs the transcription of the PTM molecule. Such a vector can remain episomal or become chromosomally integrated, as long as it can be transcribed to produce the desired RNA. Such vectors can be constructed by recombinant DNA technology methods standard in the art.

Vectors encoding the PTM of interest can be plasmid, viral, or others known in the art, used for replication and expression in mammalian cells. Expression of the sequence encoding the PTM can be regulated by any promoter known in the art to act in mammalian, preferably human cells. Such promoters can be inducible or constitutive. Such promoters include but are not limited to: the SV40 early promoter region (Benoist, C. and Chambon, P. 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), the viral CMV promoter, the human chorionic gonadotropin-$\beta$ promoter (Hollenberg et al., 1994, Mol. Cell. Endocrinology 106:111-119), etc. Any type of plasmid, cosmid, YAC or viral vector can be used to prepare the recombinant DNA construct which can be introduced directly into the tissue site. Alternatively, viral vectors can be used which selectively infect the desired target cell.

In a specific embodiment, the vectors encoding the PTM(s) of interest include recombinant conditionally replicative viruses that have been genetically engineered to replicate in cancer cells, tumor vasculature or in cells infected with pathogenic organisms. These PTM(s) are designed to interact with pre-mRNA(s) selectively expressed in cells permissive for viral replication and mediate a trans-splicing reaction resulting in the production of light producing proteins or enzymes that activate a photosensitizer and induce cell death. These PTMs may be used to enhance the potency of cell killing of conditionally replicating viruses. Alternatively, these PTMs may be used as a fail-safe mechanism to limit the replication and spread of conditionally replicating viruses.

In a specific embodiment of the invention recombinant conditionally replicative adenoviruses designed to express PTMs encoding a light producing protein or enzyme may be utilized to target selective cell death. These conditionally replicating adenoviruses may be engineered to selectively replicate in cancer cells, endothelial cells of tumor vasculature or in cells infected with a pathogenic microorganism by abrogation of viral functions essential for replication in normal cells (Bischoff et al. 1996. Science 274: 373-376), or by transcriptional regulation of viral genes essential for replication by cell-selective promoters (Hallenbeck et al., 1999 Human Gene Therapy 10:1721-1733).

In a specific embodiment of the invention, the conditionally replicative adenoviruses encoding the PTM(s) of interest may be engineered to alter the mechanism of the virus/cell interaction thereby targeting selective adenovirus infection to a specific cell type of interest, i.e., a cancer cell or infected cell. For example, the structure of the adenovirus receptor binding components, such as the viral capsid, may be genetically engineered to promote specific interactions between engineered capsids and target cell surface molecules expressed in the target cell. For example, a receptor binding ligand can be linked to a capsid protein through genetic engineering of the capsid gene. Alternatively, biospecific chemical conjugates may be linked to the adenovirus particles. (See, Adenoviral Vectors for Gene Therapy, Curiel and Douglas, eds. 2002, Academic Press).

In a specific embodiment of the invention, the PTM(s) of interest may be encoded by recombinant conditionally replicative adenoviruses engineered to express PTM(s) that mediate trans-splicing to pre-mRNAs selectively expressed in cancer or infected cells to produce adenoviral protein(s) essential for viral replication. The recombinant adenovirus is thus engineered to encode PTMs capable of producing upon trans-splicing both (i) a light producing enzyme and (ii) an adenovirus protein. Alternatively, a single PTM may be designed to express an adenovirus/light producing enzyme fusion protein, wherein the adenovirus portion of the fusion protein retains its ability to provide complementing activity and the light producing enzyme portion retains its ability to generate light. Such recombinant adenoviruses may be generated using a variety of different cloning methods known to those of skill in the art including those described in U.S. patent application Ser. No. 10/434,727, which is incorporated herein in its entirety, and in Adenoviral Vectors for Gene Therapy, Curiel and Douglas, eds. 2002, Academic Press and Ausubel et al. (eds.), 1993, Current Protocols in Molecular Biology, John Wiley & Sons, NY; and Kriegler, 1990, Gene Transfer and Expression, A Laboratory Manual, Stockton Press, NY. In preferred embodiments of the invention, the adenoviruses are type 2, 5, 9 or 35 adenoviruses.

For both in vitro or homologous recombination, transfection methods that may be utilized for the delivery of a nucleic acid molecule into the complementing cell include methods such as electroporation, lipofection, or calcium phosphate mediated transfection. The recombinant adenovirus may then isolated through plaque purification.

In addition, methods for adenoviral preparation based on homologous recombination of two plasmids using yeast artificial chromosomes or bacteria may also be utilized to generate the recombinant adenoviruses of the invention. U.S. patents disclosing preparation of recombinant adenoviruses include: U.S. Pat. Nos. 5,962,313; 5,962,311; 5,952,221; 5,932,210; 5,928,944; 5,922,576; 5,919,676; 5,891,690; 5,885,808; 5,880,102; 5,877,011; 5,871,982; 5,869,037; 5,858,351; 5,851,806; 5,843,742; 5,837,484; 5,820,868; 5,789,390; 5,756,283; 5,747,072; 5,731,172; 5,700,470; 5,670,488; 5,616,326; 5,589,377; 5,585,362; and 5,354,678. Other references of interest include Berkner, et al. (1983, Nucleic Acids Res. 11, 6003-6020); Bett, et al. (1994, Proc. Natl. Acad. Sci. USA, 91, 8802-6); Chartier, et al. (1996, J. Virol. 70, 4805-4810); Crouz et et al. (1997, Proc. Natl. Acad. Sci. USA, 94, 1414-1419); Gilardi et al. (1990, FEBS Lett. 267, 60-2); He, et al. (1998, Proc. Natl. Acad. Sci. USA, 95, 2509-2514); Ketner, et al. (1994, Proc. Natl. Acad. Sci. USA, 91, 6186-6190; Miyake, et al. (1996, Proc. Natl. Acad. Sci. USA, 93, 1320-1324); and Rosenfeld, et al. (1991, Science. 252, 431-4) the

5.3. Uses and Administration of Trans-Splicing Molecules

The compositions and methods of the present invention will have a variety of different applications including targeting of cell lysis to cancer cells or cells infected with or adjacent to an infectious agent. The methods of the invention comprise contacting a cell, or tissue of a host, with a PTM of the invention or a nucleic acid molecule encoding such a PTM. If the target pre-mRNA is expressed in the cell, a trans-splicing reaction will occur resulting in the production of a chimeric mRNA molecule capable of encoding a light emitting protein or enzyme that produces light in the presence of substrate. In addition, the cell is further contacted with a photosensitizer wherein co-localization of the photosensitizer, the light producing enzyme and substrate, results in production of cytotoxic substances, such as oxygen-related intermediates. Such photosensitizers include, but are not limited to rose bengal, hypercin, haematoporphyrin (HPD) porfimer sodium, benzoporphyrin derivative monoacid ring A (BPD-MA), meta-tetrahydroxyphenylchlorin (MTHPC), 5-aminolevulinec acid (5-ALA), 5-ALA-methylester, 5-ALA benzylester, 5-ALA hexylester, tin ethyl etipurpurin (SnEt2), boronate protoporphyin, 2-(1-hexyloxyethyl)-2-devinyl pyropheophorbide-alpha (HPPH), lutetium texaphyrin, phthalocyanine-4 and taporphin sodium. Since each photosensitizer is stimulated by a specific wavelength of light, the selection of photosensitizer to be used will depend on the wavelength of light produced by the protein or light producing enzyme/substrate reaction. Other substances can be activated or precipitated by light, including metal salts, such as silver nitrate and others which are well known in the photographic arts. Toxicity can by mediated directly by the metal itself, or indirectly by acting as a co-factor in an enzymatic reaction, or by activation of the metal by externally applied neutrons (Merril, 1990 Nature 343:779-80).

Various delivery systems are known and can be used to transfer the compositions of the invention into cells, e.g. encapsulation in liposomes, microparticles, microcapsules, recombinant cells capable of expressing the composition, receptor-mediated endocytosis (see, e.g., Wu and Wu, 1987, J. Biol. Chem. 262:4429-4432), construction of a nucleic acid as part of a virus or other vector, injection of DNA, electroporation, calcium phosphate mediated transfection, etc.

Any of the methods for gene delivery into a host cell available in the art can be used according to the present invention. For general reviews of the methods of gene delivery see Strauss, M. and Barranger, J. A., 1997, Concepts in Gene Therapy, by Walter de Gruyter & Co., Berlin; Goldspiel et al., 1993, Clinical Pharmacy 12:488-505; Wu and Wu, 1991, Biotherapy 3:87-95; Tolstoshev, 1993, Ann. Rev. Pharmacol. Toxicol. 33:573-596; Mulligan, 1993, Science 260: 926-932; and Morgan and Anderson, 1993, Ann. Rev. Biochem. 62:191-217; 1993, TIBTECH 11(5):155-215. Exemplary methods are described below.

In a specific embodiment, the nucleic acid is directly administered in vivo, where it is expressed to produce the PTM. This can be accomplished by any of numerous methods known in the art, e.g., by constructing it as part of an appropriate nucleic acid expression vector and administering it so that it becomes intracellular, e.g. by infection using a defective or attenuated viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, J. Biol. Chem. 262:4429-4432).

In a specific embodiment, an adenoviral vector that contains the PTM can be used. For example, a adenoviral vector can be utilized that has been modified to delete adenoviral sequences that are not necessary for packaging of the viral genome and which expresses a PTM capable of expressing a light producing enzyme upon trans-splicing. Alternatively, lentiviral, retroviral or adeno-associated viral vectors, among others can be used for gene delivery to cells or tissues. (See, Kozarsky and Wilson, 1993, Current Opinion in Genetics and Development 3:499-503 for a review of adenovirus-based gene delivery).

Another approach to PTM delivery into a cell involves transferring the PTM to cells in tissue culture by such methods as electroporation, lipofection, calcium phosphate mediated transfection, or viral infection.

The present invention also provides for compositions comprising an effective amount of a PTM or a nucleic acid encoding a PTM, and an acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the PTM is administered. Examples of suitable pharmaceutical carriers are described in "Remington's Pharmaceutical sciences" by E. W. Martin.

In specific embodiments, pharmaceutical compositions are administered: (1) in diseases or disorders involving the expression of a cancer selective target pre-mRNA, e.g., tumor cells; (2) in diseases or disorders where cells are infected with an infectious agent and express a target pre-mRNA encoded by or produced in reaction to the presence of infectious agent or (3) diseases or disorders arising from the activity of a specific cell type.

In a specific embodiment, it may be desirable to administer the pharmaceutical compositions of the invention locally to the area in need of treatment, e.g., the site of the tumor. This may be achieved by, for example, and not by way of limitation, inhalation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Other control release drug delivery systems, such as nanoparticles, matrices such as controlled-release polymers, hydrogels.

The methods of the invention comprise administration of both (i) the PTMs of the invention, i.e., those PTMs capable of expressing a light producing protein or enzyme, (ii) when an enzyme is utilized, an enzyme substrate and (iii) a photosensitizer wherein co-localization of cells expressing the light producing protein or enzyme/substrate and the photosensitizer results in activation of the photosensitizer. Such activation will result in production of cytotoxic oxygen-related intermediates capable of mediating cell death.

The extent of cytotoxicity is multifunctional and will depend on the type of photosensitizer used, its location, the dose administered, the total dose of light, oxygen availability and the time between administration of the photosensitizer and light exposure. Such parameters can be determined using procedures well known to those of skill in the art.

The PTMs of the invention will be administered in amounts which are effective to produce the desired effect in the targeted cell, e.g., cell lysis. Effective dosages of the PTMs can be determined through procedures well known to those in the art which address such parameters as biological half-life, bioavailability and toxicity. In addition, the presence of substrate is required for enzyme mediated generation of light In addition, photosensitizers are administered in amounts which are effective to produce the desired effect in the targeted cell, e.g., cell lysis. Effective dosages of the photosensitizers can also be determined through procedures well known to those in the art which address such parameters as biological half-life, bioavailability and toxicity.

The amount of the composition of the invention which will be effective will depend on the nature of the disease or disorder being treated, and can be determined by standard clinical techniques. In addition, in vitro assays may optionally be employed to help identify optimal dosage ranges.

The present invention is not to be limited in scope by the specific embodiments described herein. Indeed, various modifications of the invention in addition to those described herein will become apparent to those skilled in the art from the foregoing description and accompanying Figures. Such modifications are intended to fall within the scope of the appended claims. Various references are cited herein, the disclosure of which are incorporated by reference in their entireties.

6. Example: Trans-Splicing of Luciferase into Exogenously Expressed Genes

The following example describes the production of PTMs designed to encode a light producing enzyme.

6.1. Materials and Methods

6.1.1. Design and Construction of PTMs

The binding domain of PTMs can be assembled from either PCR products or annealed oligonucleotides. The coding sequence for firefly luciferase is generated by PCR or directly cloning from commercially available plasmid cDNA (Promega). To reduce the possibility of self-expression of the PTM prior to trans-splicing, the initiator AUG codon may be eliminated from the coding sequence during PCR amplification or cloning. As an example Luc-PTM1, shown in FIG. 3, consists of an antisense target binding domain of 100-200 nt complementary to β-HCG6 intron 1, a spacer sequence, a yeast branchpoint consensus sequence (UACUAAC) (SEQ ID NO. 3), an extensive polypyrimidine tract (12-15 pyrimidines), a 3' acceptor site (AG dinucleotide) followed by the complete coding for firefly luciferase minus the initiator codon. One or more nucleotides may be added or removed to insert the coding sequence into the proper reading frame, so that upon trans-splicing, the luciferase gene will be in the translational frame with the remaining exons of the target pre-mRNA. Unique restriction sites are placed between each of the PTM elements, facilitating the replacement of individual elements. In addition, the binding domain may contain alternate sites that initiate transcription out of frame from the reporter gene thereby preventing translation and expression of unspliced PTMs.

Optimization of PTMs. A number of approaches can be taken to improve the characteristics of luciferase PTMs as described below.

Binding domain: Several different forms of binding domain can be utilized. Using lacZ as a pre-screening model (FIG. 5) it was demonstrated that some PTMs with longer binding domains trans-spliced with higher frequency to the intended target pre-mRNA compared to PTMs with shorter binding domain (Puttaraju et al., 2001 Molecular Therapy 4:105-14). This data suggest that location, length and number of binding domains may increase the interaction of the PTM with the target. The increased interaction between the target and PTM can enhance both the efficiency and specificity of trans-splicing reaction.

Initially, PTMs with binding domains spanning 50-200 nucleotides are constructed and assayed. Safety PTMs with stem loop binding domains may also be produced. Based on the efficiency of the trans-splicing reactions, if necessary, binding domains longer than this (200-400 nt) can be utilized. Binding domains can also be designed to target different regions of the same intron, e.g. binding domains close to the donor vs. the acceptor site, or binding domains targeted to completely different introns.

Screening for PTM cis-splicing: To reduce the possibility of cis-splicing in the trans-splicing domain (TSD) of the PTM prior to target binding, TSD sequences are analyzed for the presence of potential 5' and 3' cryptic splice sites (GU-AG and AT-AC, U12 type introns) prior to construction of the binding domain. This is especially important for the linear binding domain PTMs (see below) because their intended splice sites may be available for binding splicing factors at all times. For each instance of single sites in the Binding Domain (BD) or spacer that could potentially be used as a cryptic 5' splice site are usually altered from GT to AT or other nucleotide combination with lowered potential to act as a 5' splice donor. For each situation a single site in the TSD that could potentially be used as a 3' cryptic splice site is usually altered from TAG/G to TTGC. The PTM can be screened by RT-PCR to check for the presence of major products (cis or trans) of unexpected size. PTM coding sequences may also be screened and altered if necessary in a similar manner to add or alter splicing enhancers or other sequences which can modulate splicing.

3' splice elements. 3' splice elements including the branchpoint (BP), the polypyrimidine tract (PPT) and a 3' acceptor site (AG dinucleotide) may also be included. Trans-splicing can be modulated by changing the sequence of the BP and the length and composition of the PPT. A yeast consensus branchpoint sequence UACUAAC (SEQ ID NO. 4) provides a greater rate of trans-splicing in mammalian cells (Puttaraju et al., 1999 Nature Biotechnology 17:246-52).

Modulating specificity with "safety" stems. Initial experiments can be performed with "linear" PTMs to maximize the trans-splicing efficiency. Linear PTMs have a binding domain designed to exist predominately in a single stranded configuration to maximize base pairing to target and trans-splicing efficiency. To achieve a higher degree of targeting specificity and trans-splicing, the trans-splicing domain is designed to include intra-molecular stems (termed 'safety PTM') designed to mask the 3' splicing elements carried in the PTM from spliceosomal components prior to target binding. Base pairing between free portions of the PTM binding domain with the target is thought to facilitate the unwinding of the safety stem, allowing the splicing factors access to bind to the splice site and initiate trans-splicing. A schematic drawing of the safety mechanism is illustrated in FIG. 4. An array of safety PTM designs are constructed and tested by varying the strength of the safety stem and assessing trans-splicing efficiency and specificity. For example, a safety PTM targeting the CFTR pre-mRNA has been designed with equivalent efficiency in trans-splicing as its parental PTM with improved specificity (Mansfield et al, 2000 Gene Therapy 7:1885-95).

Untranslated regions. Modification of 3' UTR and RNA processing signals are also carried out to increase RNA processing and stability. To increase the stability of trans-spliced messages and ultimately the level of luciferase activity, alternative polyadenylation signals may be engineered in the 3' untranslated sequence. To maximize the efficiency of 3' end cleavage and polyadenylation of trans-spliced mRNA, each PTM construct can be modified by including GT rich sequences (consensus YGTGTTYY) (SEQ ID NO. 5) downstream of the poly-A signal. This consensus, initially identified in herpes simplex virus genes, has been shown to be present in a large number of mammalian genes. Other modifications are also possible.

6.1.2. Cell Models

The PTM modifications described above are tested in the following cell based models. HPV infected/expressing cell lines including CaSki and SiHa cells are cervical cancer cell lines that express high and low levels of HPV RNA, respectively. β-HCG6 cell lines include H1299 which is a lung adenocarcinoma cell line that expresses low levels of target transcript. JEG-3 is a coriocarcinoma cell line that expresses considerably higher levels of β-HCG6 mRNAs. EGFR expressing cell lines include A431, an epidermoid carcinoma cell line that overexpresses EGFR and MCF7; an epithelial breast cancer cell line is used extensively in cancer research. In addition, Eccles et al., has published on a variety of tumor cell lines that have expressed varying levels of EGFR(O-Charoenrat et al., 2000 Int J. Cancer 86:307-17).

6.1.3. Assaying for Trans-Splicing: Targeting Endogenous Transcripts

Cells are transfected with PTM plasmids using Lipofectamine or TransFast reagents. Trans-splicing efficiency and specificity is assessed by performing luciferase activity assays and RT-PCR analysis of cells (transiently transfected or neomycin selected populations).

Luciferase activity assays. Trans-splicing mediated luciferase activity is initially monitored in cell extracts using luciferase assay reagents (Promega). If necessary, dual reporters are used as a means to measure the specificity of trans-splicing. This approach provides an internal control that is useful to account for the experimental variations caused by differences in cell viability, transfection efficiency, and cell lysis efficiency. The studies are performed with luciferase based PTMs including, for example, firefly and Renilla luciferases. Each marker has distinct kinetics and emission spectra, dissimilar structure and different substrate requirements, properties that make it possible to selectively discriminate between their respective bioluminescent reactions. Controls are performed to exclude the possibility that chimeric products between luciferase and targets are not being generated by recombination events.

Transfected cells are imaged using a CCD low-light monitoring system. In addition, trans-splicing efficiency at the RNA level is determined by real time quantitative RT-PCR analysis of total RNA samples using target and PTM specific primers.

It may be more efficient to initially select the best PTM candidates for the pre-mRNA targets, using cell lines that express the target RNA from a stable integrated mini-gene construct. The advantages of this system include the following: (i) the cell lines express target RNA from a genomic locus recapitulating the endogenous system, (ii) the cells are easy to transfect, and (iii) high levels of target transcript is produced, making it quicker and easier to assess differences in efficiency and specificity between PTMs. Cell lines that express different levels of the target pre-mRNA or use inducible promoters to modulate expression level may also be used. Inducible promoters will facilitate the determination of sensitivity of trans-splicing and correlation of target mRNA concentration to luciferase signal.

A simple pre-screening model based on the β-galactosidase repair model (Puttaraju et al., 2001 Mol Ther. 4:105-14) (FIG. 5A) can also be utilized. This system involves the insertion of the target introns from β-HCG6, HPV or EGFR into a mutant luciferase gene. The target is established in a stable cell line or cotransfected with PTMs. Efficiency will be quickly assessed by RT-PCR and luciferase activity assays. This type of system has proved extremely useful as a pre-screen for PTM binding domain sequences (Puttaraju et al., 2001 Mol Ther. 4:105-14). Alternatively, libraries with greater complexities may be screened using methods described in the provision patent application U.S. 60/420,498 filed on Oct. 23, 2002.

7. Example: Luciferase Model for Trans-Splicing

To evaluate the potential use of spliceosome mediated RNA trans-splicing for expression of a light producing enzyme or protein, a luciferase model was developed. To quantify the level of luciferase generated by trans-splicing in cells and small animal models, a pre-mRNA target was constructed that expressed part of the synthetic Renilla or Firefly luciferase sequence, coupled to the coding sequences for HPV E7 and the sequence of HPV immediate upstream of E7 from the human papilloma virus (HPV) (FIG. 6). The chimeric pre-mRNA target undergoes normal cis-splicing to produce an mRNA but no luciferase activity. A pre-trans-splicing molecule (PTM) was engineered that should base pair with the target intron and trans-splice the 3' luciferase 'exon', into the target producing full length luciferase mRNA capable of producing luciferase activity (FIG. 7 and 8). This PTM (Luc-PTM13) contains an 80 bp targeting domain that is complementary to intron 1 of HPV mRNA, a branchpoint (UACUAAC) (SEQ ID NO. 6) and polypyrimidine tract, AG dinucleotide acceptor followed by 3' hemi luciferase 'exon'. This region was selected based on the results targeting this clinically relevant splice site in HPV mRNA, where as high as 70% trans-splicing efficiency was achieved in cell culture models. A splice mutant was also constructed by deleting both the branchpoint and polypyrimidine sequences. Using these constructs, accurate trans-splicing of luciferase PTM13 (Luc-PTM13) into HPV-LucT1 target in human cells was demonstrated. Human embryonic kidney cells were transfected with either target, PTM alone as controls or co-transfected with both target and PTM expression plasmids. In a separate transfection target and splice mutant PTM were co-transfected. RT-PCR analysis of total RNA using target and PTM specific primers produced the expected trans-spliced (435 bp) product only in cells that contained both target and PTM but not in controls (target, PTM alone and target+splice mutant PTM) (FIG. 9).

Direct sequence of this RT-PCR product confirmed the accurate trans-splicing between the target and PTM (FIG. 10). The efficiency of trans-splicing mediated restoration of function was confirmed at the protein level by assaying for luciferase activity. The results are summarized in FIG. 11. Co-transfection of a specific target with Luc-PTM13 resulted in the repair and restoration of luciferase function that is on the order of 4-logs over the background. No luciferase activity above background was detected in controls or with splice mutant PTM suggesting that the restoration of luciferase function is due to trans-splicing (FIG. 11).

In a parallel study, PTMs that trans-splice complete luciferase coding (minus the 1st ATG codon) into the β-HCG6 pre-mRNA target were constructed. Preliminary results suggest that these PTMs are self-expressing. This was not overly surprising because these PTMs may be using one of the internal methionines contained in the coding sequence of luciferase for translation. To circumvent this the following approaches may be taken: (1) conversion of the methionines at amino acid position 8 and 27, for example, of luciferase coding sequence to isolucine; (2) adding a nuclear retention signal (U6 snRNA) at the 5' end to prevent PTM export prior to trans-splicing, and (3) designing PTMs such that they would initiate translation out-of-frame if the PTMs are exported into the cytoplasm without undergoing trans-splicing.

8. Example: Expression of Light Producing Enzymes in Cells Using Synthetic PTM RNA

8.1. Materials and Methods

8.1.1. In Vitro Transcription and Purification of RNA

Template DNA: Plasmids, pc3.1Luc-PTM13, pc3.1Luc-PTM14 and pc3.1Luc-13-BP/PPT (splice mutant PTM) containing T7 promoter were digested with Hind III restriction enzyme at 37° C. The products were extracted with buffered phenol followed by chloroform or purified using Qiaquick PCR purification kit (Qiagen). The DNA was recovered by ethanol precipitation and washed twice with 70% ethanol, air dried for 5 minutes, re-suspended with sterile water and used for in vitro transcription.

In vitro transcription: In vitro transcription was performed in 20 μl reaction using mMESSAGE mMACHINE high yield capped RNA transcription kit for capped RNA following manufacturers protocol (Ambion) and 1 μg of linearized plasmid DNA template. The reactions were incubated at 37° C. for 2-3 hours and the DNA template was destroyed by adding 1 μl of DNase 1 (2U/μl) and continuing the incubation at 37° C. for an additional 45 minutes. The poly A tail (~150-200 nt) was added to the in vitro transcribed RNA using poly A tailing kit (Ambion) by incubating the reaction with E. coli poly A polymerase and ATP by incubating at 37° C. for 60 minutes. Reactions were terminated by placing the tubes on ice and the RNAs were purified as described below.

RNA Purification: In vitro transcribed, poly A tailed RNA was purified using MEGAclear purification kit (Ambion) which is designed to remove unincorporated free nucleotides, short oligonucleotides, proteins and salts from RNA. Briefly, RNA was bound to the filter cartridge, washed with washing buffer and eluted with a low salt buffer.

8.1.2. Synthetic RNA Transfections

The day before transfection, 1×10⁶ 293T cells were plated in 60 mm tissue culture plate with 5 ml of DMEM growth medium supplemented with 10% FBS. Cells were incubated at 37° C. in a $CO_2$ incubator for 12-14 hours or until the cells are ~70-80% confluent. Before transfection, the cells were washed with 2 ml Opti-MEM 1 reduced serum medium. The RNA-Lipid complexes were prepared by adding 1.7 ml of Opti-MEM 1 into 2 ml tube followed by 8 μl of DMRIE-C transfection reagent (Invitrogen) and mixed briefly. To the above mix, known amount of the in vitro transcribed, poly A tailed and purified RNA was added, vortexed briefly and immediately added drop wise on to the cells. The cells were incubated for 4 hours at 37° C. and then the transfection medium was replaced with complete growth medium (DMEM with 10% FBS). After incubating for an additional 24-48 hours, the plates were rinsed with PBS once, cells harvested and total RNA was isolated using MasterPure RNA purification kit (Epicenter Technologies, Madison, Wis.). Contaminating DNA in the RNA preparation was removed by treating with DNase 1 at 37° C. for 30-45 minutes and the product RNA was purified as recommended in the kit.

8.1.3. Reverse Transcription and Polymerase-Chain Reaction (RT-PCR)

Total RNA (2.5 μg) from the transfections was converted to cDNA using the MMLV reverse transcriptase enzyme (Promega) in a 25 μl reaction following the manufacturers protocol with the addition of 50 units RNase Inhibitor (Invitrogen) and 200 ng Luc-11R PTM specific primer (5'AAGCTTTTACTGCTCGTTCTTCAGCACGC) (SEQ ID NO. 7). cDNA synthesis reactions were incubated at 42° C. for 60 minutes followed by incubation at 95° C. for 5 minutes. This cDNA template was used for PCR reactions. PCR amplifications were performed using 100 ng of primers and 1 μl template (RT reaction) per 50 μl PCR reaction. A typical reaction contained ~25 ng of cDNA template, 100 ng of primers: Luc-33R (5'-CAGGGTCGGACTCGATGAAC) (SEQ ID NO. 8) and, Luc-34F, 5'-GGATATCGCCCTGAT-CAAGAG) (SEQ ID NO. 9) 1×REDTaq PCR buffer (10 mM Tris-HCl, pH 8.3, 50 mM KCl, 1.1 mM $MnCl_2$ and 0.1% gelatin), 200 μM dNTPs and 1.5 units of REDTaq DNA polymerase (Sigma, Saint Louis, Mo.). PCR reactions were performed with an initial pre-heating at 94° C. for 2 minutes 30 seconds followed by 25-30 cycles of 94° C. for 30 seconds (denaturation), 60° C. for 36 seconds (annealing) and 72° C. for 1 minute (extension) followed by a final extension at 72° C. for 7 minutes. The PCR products were then analyzed on a 2% agarose gel and the DNA bands were visualized by staining with ethidium bromide.

8.1.4. Assay for Renilla Luciferase Activity 48 hours post-transfection the cells were rinsed once with 1× phosphate buffered saline (PBS) and harvested following the standard procedures. The cell pellet was re-suspending in 100 μl of lysis buffer, lysed and Renilla Luciferase activity was measured by the Renilla Luciferase assay system (Promega, Madison, Wis., USA) using a Turner 20/20 TD luminometer.

8.2. Results

Using in vitro synthesized PTM RNA as genetic material, it was demonstrated that synthetic PTMs could be utilized for gene expression of light producing enzymes in human cells. As described above, to quantify the level of synthetic Renilla luciferase activity generated by trans-splicing, a synthetic Renilla luciferase model system was developed. (See FIG. 8). To demonstrate the use of synthetic PTMs, Luc-PTM13, Luc-PTM14, Luc-13 ΔBP/PPT (FIG. 12) and the HPV-Luciferase chimeric target (HPV-LucT1) RNAs (capped and poly A tailed) were synthesized using bacteriophage T7 RNA polymerase in vitro. Contaminating DNA was destroyed by treating with RNase free DNase 1, the RNA was purified and used for transfections. The transfections were performed as described above using DIMRE-C reagent. 48 hours post-transfection, total cellular RNA was isolated using Master-Pure RNA isolation kit and analyzed by RT-PCR using target (Luc-34F) and PTM (Luc-33R) specific primers as described above. As shown in FIG. 13, no product was detected with RNA samples from mock, target or PTM alone control transfections (lanes 1-4). RNA from cells that were co-transfected with the HPV-luciferase target and a functional PTM produced a specific 298 bp product (FIG. 13, lanes 6 and 7). No such product was detected with RNA from cells that were co-transfected with target and splice mutant PTM (Luc13ΔPB/PPT), which does not contain a functional 3' splice site (no branchpoint and polypyrimidine tract) (lane 5). These results not only demonstrate the importance of both the branchpoint and the pyrimidine tract for trans-splicing but also confirm that the production of the 298-bp product is due to trans-splicing. The accuracy of trans-splicing between HPV-LucT1 target pre-mRNA and Luc-PTM13 and Luc-PTM14 was confirmed by direct sequencing of the RT-PCR product.

The efficiency of trans-splicing mediated mRNA repair and restoration of synthetic Renilla luciferase function was confirmed by assaying for enzymatic activity. As shown in FIG. 14, the synthetic Renilla luciferase activity in target or PTM alone control transfections is essentially at the background level that is observed in mock transfection. Co-transfection with a specific HPV-luciferase target (HPV-LucT1) along with Luc-PTM13 or Luc-PTM14 resulted in the repair of the target pre-mRNA and restored synthetic Renilla luciferase activity to a level that is 2000-fold over the background observed with a splice mutant PTM under similar experimental conditions. These results demonstrated the successful use of synthetic PTMs for targeting expression of light producing enzymes.

9. Example: Expression of Light Producing Enzymes Through 3' Exon Replacement

The PTM contains the complete coding of firefly luciferase minus the AUG start codon. The trans-splicing domain consists of a set of strong 3' splice elements (including a yeast consensus branchpoint, a long pyrimidine tract and a 3' acceptor site), a spacer sequence and a 125 nucleotide binding domain complementary to the 3' end of the intron between exons E6 and E7 of human papilloma virus (HPV) (FIG. 15). The trans-splicing model for this PTM is shown in FIG. 16. To prevent PTM translation in the absence of trans-splicing a number of methionines in the 5' end of the PTM coding were modified. This was carried out by site directed mutagenesis in which methionines were converted to codons that were considered conservative substitutions (based on amino acid alignments with other luciferase genes).

One potential problem is that in some instances the PTM itself may be translated. Since the 3' exon replacement luciferase PTMs include the complete luciferase coding (minus the AUG initiator codon) and not a fragment of the full-length cDNA (as is the case with most previous PTMs) there could be a problem with un-spliced PTM being exported into cytoplasm and translation in the absence of trans-splicing. Thus, a Renilla luciferase based PTM that can perform 5' exon replacement was generated. This form of PTM has the potential advantage of reduced PTM translation since the constructs can be engineered without a polyA signal. In the absence of this signal the RNA cannot be properly processed and translated.

The structure of the Renilla luciferase 5' exon replacement PTM is shown in FIG. 18. It consists of the full coding for Renilla luciferase split into two "exons", separated by a mini-intron. The trans-splicing domain contains a consensus 5' donor site, a short spacer sequence and a binding domain complementary to the 3' end of the intron between exons E6 and E7 of the human papilloma virus (HPV). The trans-splicing model for this PTM is shown in FIG. 19.

Firefly luciferase PTMs were cotransfected with or without a HPV mini-gene target (see FIG. 16) in 293T cells. Cells were harvested after 48 hours and assayed for luciferase activity. These experiments showed that samples with target produced ~2 fold higher activity indicating that trans-splicing was occurring with the mini-gene target and that there was reduced translation of the PTM (see FIG. 17).

10. Example: Hemi-Reporter Model Targets and PTMS

FIG. 20 depicts the hemi-reporter model targets and PTMs used for expression of light producing enzymes. The mini-gene pre-mRNA targets consists of the 5' portion of humanized Renilla luciferase (hRluc) which acts as a "5' exon", coupled to the E6-E7 intron region and adjacent E7 coding sequence of human papilloma virus (HPV16).

As depicted in FIG. 20, PTMs consisting of the remainder of the light producing enzyme were engineered to repair the mRNA and restore function. Several PTMs were constructed consisting of a "binding domain" complementary to the HPV target intron, a 3' splice site (consisting of a BP, PPT and acceptor AG nucleotide), and the remainder hRL sequence as a 3' exon. The only difference between the PTMs is the size of the "3' exon" which ranged from 255 nt to 50 nt. Through its binding domain, the PTM is expected to base pair and co-localize with the target pre-mRNA. This facilitates trans-splicing between the splice sites of the target "5' exon" and the "3' exon" of the PTM, repairing the target mRNA and producing enzymatic activity.

To compare the trans-splicing efficiency of PTM14, PTM28 and PTM37, human embryonic kidney (293T) cells were transfected with target and with the PTMs described above. 48 hours post-transfection, total cellular RNA was isolated and analyzed by RT-PCR using a target and a PTM specific primer. Based on a semi-quantitative estimation, Luc-PTM28 and Luc-PTM37 showed more efficient trans-splicing (~2-4 fold) compared to Luc-PTM14 (FIG. 21). Here, a smaller PTMs trans-spliced more efficiently than the larger PTMs.

The efficiency of trans-splicing mediated mRNA repair and restoration of Luciferase function was confirmed by assaying for enzymatic activity. As demonstrated in FIG. 22, Luciferase activity in target or PTM alone control transfections is essentially at the background level that is observed in mock transfection. Co-transfection with a specific HPV-luciferase hemi-reporter target, HPV-LucT1, HPV-LucT2 or HPV-LucT3 along with Luc-PTM14, Luc-PTM28 or Luc-PTM37, respectively, resulted in the efficient repair of pre-mRNA targets and restored luciferase activity on the order of 3-4 logs over background (FIG. 22). Luciferase activity produced by Luc-PTM37 is ~3 fold higher compared to Luc-PTM14.

Figure 23A:
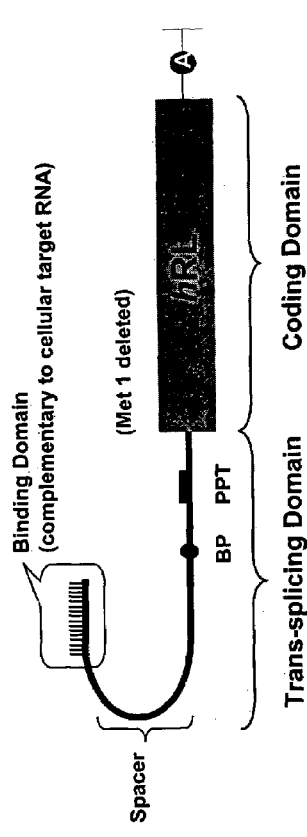
Figure 23B:
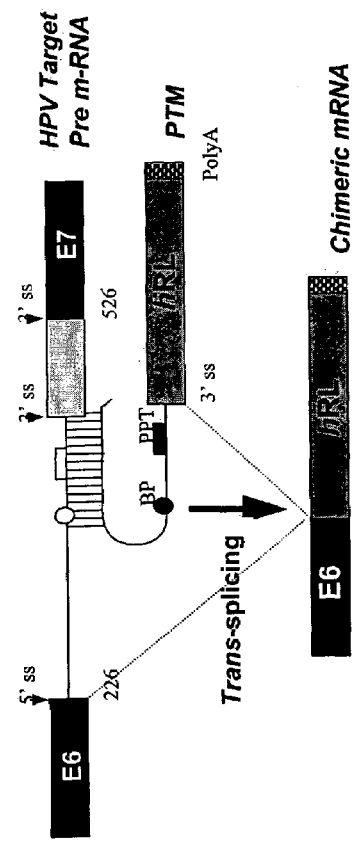

11. Example: Targeting Gene Expression Using Full-Length PTMs Encoding a Light Producing Enzyme The full length PTM (Luc-PTM27) contains the complete coding sequence for humanized Renilla Luciferase (hRL) minus the AUG start codon. The trans-splicing domain consists of a strong 3' splice element (including a yeast consensus branch point (BP), a long pyrimidine tract (PPT) and a 3' acceptor site), a spacer sequence and a 80 nucleotide binding domain (BD) complementary to the 3' end of the intron between exons E6 and E7 of human papilloma virus (HPV-16) (FIG. 23A). Schematic illustration of trans-splicing mediated restoration of Luciferase function is shown in FIG. 23B.

Full-length PTM was co-transfected with or without a HPV mini-gene target into 293 cells. Cells were harvested 48 hr post-transfection and assayed for luciferase activity. The results depicted in FIG. 24 demonstrate that cells with target produced ~3 fold higher luciferase activity indicating the proper trans-splicing between the HPV mini-gene target and the PTM. The results also indicate that this particular PTM (in the absence of target) does express the light producing enzyme which may be partly due to (i) direct translation of the PTM, (ii) PTM cis-splicing and translation or (iii) non-specific trans-splicing.

A Luciferase splice mutant PTM was constructed to determine whether the restoration of Luciferase function is due to RNA trans-splicing (FIG. 25B). The PTM is a derivative of Luc-PTM38 (FIG. 25A) in which the 3' splice elements such as BP, PPT and the acceptor AG dinucleotide were modified by PCR mutagenesis and were confirmed by sequencing.

293T cells were co-transfected with or without HPV mini-gene target along with either a functional or splice mutant PTM. Cells were harvested after 48 hours and assayed for Luciferase function. As depicted in FIG. 26, the Luciferase activity in cells transfected with splice mutant PTM and with or without HPV mini-gene target are similar to the background observed with mock transfection. In contrast, cells that were co-transfected with Luc-PTM38 (functional PTM) and with target produced ~4-5 fold more Luciferase activity compared to PTM38 alone.

12. Example: Targeting of Gene Expression of Gene Expression

The results described below demonstrate the successful in vivo target expression of light producing enzymes through spliceosome mediated RNA trans-splicing. The experimental results described below indicate the successful development of PTMs that can target and trans-splice sequences encoding a light producing enzyme into an endogenous pre-mRNA of interest, including those associated with diseases such as infectious diseases and proliferative, neurological and metabolic disorders, thereby producing a chimeric mRNA encoding the light producing enzyme through spliceosome mediated RNA trans-splicing. This approach provides methods for targeting expression of a light producing enzyme to a specific cell type.

A pre-mRNA target was constructed that had the 5' part of hRluc sequence, coupled to the coding sequence for human papilloma virus (HPV) E6 & E7 and the intronic sequences immediately upstream. Cis-splicing of HPV-LucT1 does not produce any hRluc activity. Several PTMs carrying the remaining hRluc sequence as a 3' exon were genetically engineered. Through its targeting domain, the PTM base pairs with the HPV-LucT1 intron facilitating the trans-splicing of the 3' luciferase exon, thereby repairing the pre-mRNA target and subsequently restoring enzymatic activity. The PTMs contain a targeting domain that is complementary to the intron in HPV-LucT1, a branch point (BP), pyrimidine tract (Py) and a 3' splice acceptor site. For in vivo applications, PTMs were complexed with transferrinpolyethylineamine (Tf-PEI) (Hildebrandt, I. et al., 2002, Molecular Therapy 5:S421).

To test in vivo targeting of gene expression, $2.5 \times 10^6$ 293T cells were transfected with PTM14, target or target+PTM14 (10 µg/plate) on Day 1. The ratio of PTM to target was 1:1. On Day 2, cells were washed with PBS and $1 \times 10^6$ cells were injected subcutaneously into a mouse. On Day 3, cells within the mice were imaged by use of a cooled CCD camera immediately after injection of Coelenterazine substrate via tail vein (Bhaumik & Gambhir, 2002, Proc. Natl. Acad. Sci. USA 99:377-382). As depicted in FIG. 27, no signal was detected in cells transfected with target (T) or PTM (P) alone. In contrast, cells co-transfected with target and PTM produced high signal levels (T+P). The results clearly indicate successful RNA trans-splicing to target gene expression in vivo.

In a second experiment, $2.5 \times 10^6$ N2a cells were transiently transfected with HPV-LucT1 target plasmid (10 µg) on Day 1. On Day 2, cells were washed with PBS and $\sim 5 \times 10^6$ cells were implanted into 3-4 week old nude mice. Following implantation, 50 µg of Luc-PTM-14 conjugated with transferring-polyethylineamine (Tf-PEI) was then injected into the mouse via the tail vein. On Day 3, 80 µg of Coelenterazine substrate was injected via tail vein and the mice were imaged immediately for 5 min using a cooled CCD camera. As depicted in FIG. 28 tumors expressing HPV-LucT1 pre-mRNA target produced signals that were statistically significant (P<0.05)., In contrast, no signal was detected with N2a control tumor. The results depicted in FIG. 28 demonstrate targeting of gene expression in vivo following IV PTM delivery into target cells.

The present invention is not to be limited in scope by the specific embodiments described herein. Indeed, various modifications of the invention in addition to those described herein will become apparent to those skilled in the art from the foregoing description and accompanying Figures. Such modifications are intended to fall within the scope of the appended claims. Various references are cited herein, the disclosure of which are incorporated by reference in their entireties.

We claim:

1. A isolated cell comprising a nucleic acid molecule wherein said nucleic acid molecule comprises:
   (a) one or more target binding domains that target binding of the nucleic acid molecule to a target pre-mRNA expressed within the cell;
   (b) a 3' splice region comprising a 3' splice acceptor site;
   (c) a spacer region that separates the 3' splice region from the target binding domain; and
   (d) a nucleotide sequence encoding a light producing protein or enzyme to be trans-spliced to the target pre-mRNA;
   wherein said nucleic acid molecule is recognized by nuclear splicing components within the cell and wherein the light producing protein or enzyme activates a cytotoxic photosensitizer that causes cell death.

2. The cell of claim 1 wherein the 3' splice region further comprises a branch point and a pyrimidine tract.

3. The cell of claim 1 or 2 wherein the nucleic acid molecule further comprises a 5' donor site.

4. A isolated cell comprising a nucleic acid molecule wherein said nucleic acid molecule comprises:
   (a) one or more target binding domains that target binding of the nucleic acid molecule to a target pre-mRNA expressed within the cell;
   (b) a 5' splice site;
   (c) a spacer region that separates the 5' splice site from the target binding domain; and
   (d) a nucleotide sequence encoding a light producing protein or enzyme to be trans-spliced to the target pre-mRNA;
   wherein said nucleic acid molecule is recognized by nuclear splicing components within the cell and wherein the light producing protein or enzyme activates a cytotoxic photosensitizer that causes cell death.

5. A method of producing a chimeric mRNA molecule in a cell wherein said chimeric molecule expresses a light producing protein or enzyme comprising contacting a target pre-mRNA expressed in the cell with a nucleic acid molecule recognized by nuclear splicing components wherein said nucleic acid molecule comprises;
   (a) one or more target binding domains that target binding of the nucleic acid molecule to a target pre-mRNA expressed within the cell;
   (b) a 3' splice region comprising a 3' splice acceptor site;
   (c) a spacer region that separates the 3' splice region from the target binding domain; and
   (d) a nucleotide sequence encoding a light producing protein or enzyme to be trans-spliced to the target pre-mRNA;
   under conditions in which a portion of the nucleic acid molecule is trans-spliced to a portion of the target pre-mRNA to form a chimeric mRNA within the cell within the cell wherein the light producing protein or enzyme activates a cytotoxic photosensitizer that causes cell death.

6. The method of claim 5 wherein said 3' splice region further comprises a branch point and a pyrimidine tract.

7. The method of claim 5 or 6 wherein the nucleic acid molecule further comprises a 5' donor site.

8. A method of producing a chimeric mRNA molecule in a cell wherein said chimeric molecule expresses a light producing protein or enzyme comprising contacting a target pre-mRNA expressed within the cell with a nucleic acid molecule recognized by nuclear splicing components wherein said nucleic acid molecule comprises:
   (a) one or more target binding domains that target binding of the nucleic acid molecule to a target pre-mRNA expressed within the cell;
   (b) a 5' splice site;
   (c) a spacer region that separates the 5' splice site from the target binding domain; and
   (d) a nucleotide sequence encoding a light producing protein or enzyme to be trans-spliced to the target pre-mRNA;
   under conditions in which a portion of the nucleic acid molecule is trans-spliced to a portion of the target pre-mRNA to form a chimeric mRNA within the cell within the cell wherein the light producing protein or enzyme activates a cytotoxic photosensitizer that causes cell death.

9. A method for targeting cell death comprising:
   (i) contacting said cell with a nucleic acid molecule wherein said nucleic acid molecule comprises:
      a) one or more target binding domains that target binding of the nucleic acid molecule to a target pre-mRNA expressed within the cell;
      b) a 3' region comprising a 3' splice acceptor site;
      c) a spacer region that separates the 3' splice region from the target binding domain; and
      d) a nucleotide sequence encoding a light producing protein or enzyme to be trans-spliced to the target pre-mRNA; wherein said nucleic acid molecule is recognized by nuclear splicing components within the cell; and
   (ii) placing a photosensitizer in close enough proximity to the cell to permit activation of the photosensitizer by the light producing enzyme, wherein said activation results in cell death.

10. The method of claim 9 wherein said 3' splice region further comprises a branch point and a pyrimidine tract.

11. The method of claim 9 or 10 wherein the nucleic acid molecule further comprises a 5' donor site.

12. A method for targeting cell death comprising:
   (i) contacting said cell with a nucleic acid molecule wherein said nucleic acid molecule comprises:
      a) one or more target binding domains that target binding of the nucleic acid molecule to a target pre-mRNA expressed within the cell;
      b) a 5' splice site;

c) a spacer region that separates the 3' splice region from the target binding domain; and d) a nucleotide sequence encoding a light producing protein enzyme to be trans-spliced to the target pre-mRNA; wherein said nucleic acid molecule is recognized by nuclear splicing components within the cell; and (ii) placing a photosensitizer in close enough proximity to the cell to permit activation of the photosensitizer by the light producing enzyme, wherein said activation results in cell death.

13. The method of claim 9, 10 or 12 further comprising contacting said cell with a substrate specific for the light producing protein or enzyme.

14. The method of claim 11 further comprising contacting said cell with a substrate specific for the light producing protein or enzyme.

15. A method for targeting cell death comprising contacting said cell with a conditionally replicative adenovirus which encodes a light producing enzyme or protein.

* * * * *